US005807729A

United States Patent [19]

Shuster et al.

[11] Patent Number: 5,807,729

[45] Date of Patent: Sep. 15, 1998

[54] METALLOPROTEASE HAVING INCREASED ACTIVITY

[75] Inventors: Jeffrey R. Shuster, Davis; Mark Madden, Pleasant Hill; Donna L. Moyer, Davis, all of Calif.; Claus Fuglsang, Copenhagen; Sven Branner, Lyngby, both of Denmark

[73] Assignees: Novo Nordisk A/S, Bagsvaerd, Denmark; Novo Nordisk Biotech, Inc., Davis, Calif.

[21] Appl. No.: 442,859

[22] Filed: May 17, 1995

Related U.S. Application Data

[60] Division of Ser. No. 398,489, Mar. 3, 1995, which is a continuation-in-part of Ser. No. 238,108, May 4, 1994.

[51] Int. Cl.[6] .............................. C12N 9/58; C12N 15/57; C12N 15/80

[52] U.S. Cl. .......................... 435/223; 435/224; 435/225; 435/252.3; 435/254.11; 435/320.1; 536/23.2

[58] Field of Search .............................. 435/252.33, 223, 435/224, 225, 320.1, 252.3, 254.11; 536/23.2

[56] References Cited

U.S. PATENT DOCUMENTS

| | | | |
|---|---|---|---|
| 3,652,399 | 3/1972 | Isono et al. | 195/62 |
| 5,288,627 | 2/1994 | Nielsen et al. | 435/223 |

OTHER PUBLICATIONS

Nakadai, T. et al. (1973) Agr. Biol. Chem. 37(12), 2695–2701.

Tatsumi, H., et al. (1991) Mol. Gen. Genet. 228, 97–103.

Jaton–Ogay, et al. (1994) EMBL Data Library entry S42894.

*Primary Examiner*—Charles L. Patterson, Jr.
*Attorney, Agent, or Firm*—Steve T. Zelson, Esq.; Cheryl H. Agris, Esq.

[57] ABSTRACT

The present invention relates to a novel metalloprotease obtainable from a fungus having increased proteolytic activity. Additionally, the invention related to isolated nucleic acid fragments encoding said metalloprotease as well as vectors, DNA constructs, and recombinant host cells comprising said nucleic acid fragments.

19 Claims, 14 Drawing Sheets

KFN 709/710:

```
GATCCTCGAATTCTCTTCAGATCTCTTCAC
    ::::::::::::::::::::::::::::::
    GAGCTTAAGAGAAGTCTAGAGAAGTGGTAC
BamHI   EcoRI     BglII     NcoI
```

```
         9        18        27        36        45        54
>
ATG CGT TTC TCG GAC TGC CTC CTC CTC ATC GGC CTA TCC AGC CTC GCT GGT GCT
M   R   F   S   D   S   L   L   L   I   G   L   S   S   L   A   G   A

        63        72        81        90        99       108
CAT CCC AGC AGA AGG GCT CCT AAT CCT TCA CCG CTG AGC AAG CGT GGC CTC GAC
H   P   S   R   R   A   P   N   P   S   P   L   S   K   R   G   L   D

       117       126       135       144       153       162
CTG GAA GCT TTT AAG CTT CCT CCC ATG GCC GAG TAC GTT CCT CAG GAC GAG GTT
L   E   A   F   K   L   P   P   M   A   E   Y   V   P   Q   D   E   V

       171       180       189       198       207       216
CCT GAT GAT GTC AGT GCC AAG GTC GTC ACC AAG CGC GCT GAT TAC ACC GAG ACT
P   D   D   V   S   A   K   V   V   T   K   R   A   D   Y   T   E   T

       225       234       243       252       261       270
GCC AAG GAC TTG GTT AAG TCG ACT TTC CCC AAG GCT ACT TTC CGT ATG GTC ACG
A   K   D   L   V   K   S   T   F   P   K   A   T   F   R   M   V   T

       279       288       297       306       315       324
GAT CAC TAT GTT GGT AGC AAC GGA ATT GCG CAT GTA AAC TTT AAG CAG ACT GTC
D   H   Y   V   G   S   N   G   I   A   H   V   N   F   K   Q   T   V

       333       342       351       360         373        383
AAC GGT ATT GAT ATC GAC AAT GCT GAT TTC AAC GTC AAC GTGGGTATTC TCAAGACTTT
N   G   I   D   I   D   N   A   D   F   N   V   N
      393        403        413         424       433       442
GGGGAGTTTG GAATGTGCTG ACATGGATAC AG ATT GGC GCT GAC GGC GAG GTC TTC TCC
                                    I   G   A   D   G   E   V   F   S

       451       460       469       478       487       496
TAC GGA AAC AGC TTC TAC GAG GGC AAG ATT CCC GGT CCT CTT ACC AAG CGT GAC
Y   G   N   S   F   Y   E   G   K   I   P   G   P   L   T   K   R   D
```

FIG.3A

```
        505          514          523          532          541          550
GAG AAA GAC CCC GTC GAC GCT CTC AAG GAC ACC GTT GAT GTT CTT TCT CTC CCC
 E   K   D   P   V   D   A   L   K   D   T   V   D   V   L   S   L   P
        559          568          577          586          595          604
GTT GAG GCT GAC AAG GCC AAG GCT GAG AAG AAG AGC AAG AAC CAC TAC ACC TTC
 V   E   A   D   K   A   K   A   E   K   K   S   K   N   H   Y   T   F
        613          622          631          640          649          658
ACT GGT ACC AAG GGT ACC GTC AGC AAG CCC GAG GCT AAG CTC ACC TAC CTT GTT
 T   G   T   K   G   T   V   S   K   P   E   A   K   L   T   Y   L   V
        667          676          685          694          703          712
GAT GAG AAC AAG GAG CTC AAG CTC ACA TGG AGA GTT GAG ACT GAT ATT GTT GAC
 D   E   N   K   E   L   K   L   T   W   R   V   E   T   D   I   V   D
        721          730          739          748          757          766
AAC TGG CTG TTG ACT TAT GTC AAT GCT GCC AAG ACT GAT GAG GTT GTT GGT GTT
 N   W   L   L   T   Y   V   N   A   A   K   T   D   E   V   V   G   V
        775          784          793                    811        821
GTT GAC TAC GTC AAT GAG GCG ACA TAC AAG GTC TA  GTACGTATTT CCATAAATTG
 V   D   Y   V   N   E   A   T   Y   K   V   Y
        831       841        851         861          870          879
ACGATTGGGA AAGAATTGAC CGTTGTATTA TAG T CCT TGG GGT GTC AAT GAT CCC TCC
                                        P   W   G   V   N   D   P   S
        888          897          906          915          924          933
AAG GGA TCT CGC TCC ACT GTT GAG AAC CCC TGG AAT CTC GCG GCC TCC GAG TTC
 K   G   S   R   S   T   V   E   N   P   W   N   L   A   A   S   E   F
        942          951          960          969          978          987
ACC TGG CTC AGC GAC GGC TCA AAC AAC TAC ACC ACA ACC CGC GGG AAC AAT GGA
 T   W   N   S   D   G   S   N   N   Y   T   T   T   R   G
        996         1005         1014         1023         1032         1041
ATT GCA CAG GTG AAT CCT TCA GGG GGC TCC ACG TAT CTG AAC AAT TAC CGT CCT
 I   A   Q   V   N   P   S   G   G   S   T   Y   L   N   N   Y   R   P
```

FIG.3B

```
     1050      1059      1068      1077      1086      1095
GAT AGC CCG TCG CTG AAG TTC GAG TAT GAT TAC TCC ACC AGC ACC ACT ACA CCC
 D   S   P   S   L   K   F   E   Y   D   Y   S   T   S   T   T   T   P

     1104      1113      1122      1131      1140      1149
ACC ACC TAC CGC GAT GCT TCC ATC GCT CAG CTT TTC TAC ACA GCC AAC AAG TAC
 T   T   Y   R   D   A   S   I   A   Q   L   F   Y   T   A   N   K   Y

     1158      1167      1176      1185      1194      1203
CAC GAC CTC CTC TAC CTT CTT GGC TTT ACC GAA CAG GCT GGT AAC TTC CAG ACC
 H   D   L   L   Y   L   L   G   F   T   E   Q   A   G   N   F   Q   T

     1212      1221      1230      1239      1248      1257
AAC AAC AAT GGC CAG GGT GGT GTA GGA AAC GAT ATG GTT ATC CTC AAC GCT CAG
 N   N   N   G   Q   G   G   V   G   N   D   M   V   I   L   N   A   Q

     1266      1275      1284      1293      1302      1311
GAC GGA AGC GGC ACC AAC AAC GCC AAC TTC GCT ACA CCC GCT GAC GGT CAG CCC
 D   G   S   G   T   N   N   A   N   F   A   T   P   A   D   G   Q   P

     1320      1329      1338      1347      1356      1365
GGC CGC ATG CGA ATG TAT CTC TGG ACA TAC AGC ACA CCC CAG CGT GAC TGC AGT
 G   R   M   R   M   Y   L   W   T   Y   S   T   P   Q   R   D   C   S

     1374      1383      1392      1401      1410      1419
TTC GAC GCT GGC GTT GTT ATC CAC GAG TAC ACT CAC GGT CTC TCC AAC CGT CTC
 F   D   A   G   V   V   I   H   E   Y   T   H   G   L   S   N   R   L

     1428      1437      1446      1455      1464      1473
ACA GGT GGC CCT GCC AAC TCG GGT TGT CTT CCC GGT GGT GAA TCC GGT GGC ATG
 T   G   G   P   A   N   S   G   C   L   P   G   G   E   S   G   G   M

     1482      1491      1500      1509      1518      1527
GGT GAG GGC TGG GGT GAC TTC ATG GCT ACT GCC ATT CAC ATC CAA TCC AAG GAT
 C       G   W                                   H   I   Q   S   K   D

     1536      1545      1554      1563      1572      1581
ACC CGC GCT AGC AAC AAG GTC ATG GGT GAC TGG GTG TAC AAC AAC GCA GCT GGT
 T   R   A   S   N   K   V   M   G   D   W   V   Y   N   N   A   A   G
```

FIG.3C 1590 1599 1608 1617 1626 1635

ATC CGA GCT TAT CCT TAC AGT ACA AGC CTT ACC ACT AAC CCT TAC ACT TAC AAG
I R A Y P Y S T S L T T N P Y T Y K 1644 1653 1662 1671 1680 1689

AGT GTT AAC AGT CTC AGT GGA GTC CAT GCT ATT GGT ACT TAC TGG GCT ACT GTT
S V N S L S G V H A I G T Y W A T V 1698 1707 1716 1725 1734 1743

CTG TAT GAG GTT ATG TGG AAC CTC ATC GAC AAG CAT GGG AAG AAT GAT GCG GAT
L Y E V M W N L I D K H G K N D A D 1752 1761 1770 1779 1788 1797

GAG CCC AAA TTC AAC AAC GGC GTT CCT ACA GAT GGC AAA TAT CTT GCT ATG AAG
E P K F N N G V P T D G K Y L A M K 1806 1815 1830 1840 1850
1860

TTA GTA GTG GAT GGC ATG TCG CT GTAAGTTGTC CCTTGGATTT GTAGGAGTTC
TTATCTAACG
L V V D G M S L 1872 1881 1890 1899 1908

TTTAATAG G CAA CCT TGC AAC CCC AAC ATG GTC CAG GCC CGA GAC GCC ATC ATC
Q P C N P N M V Q A R D A I I 1917 1926 1935 1944 1953 1962

GAC GCC GAC ACC GCT CTT ACC AAG GGA GCT AAC AAG TGC GAG ATC TGG AAG GGC
D A D T A L T K G A N K C E I W K G 1971 1980 1989 1998 2007 2016

TTT GCC AAG CGT GGT CTT GGA ACT GGT GCC AAG TAT AGT GCT TCC AGC CGT ACT
F A K R G L G T G A K Y S A S S R T 2025 2034 2043 2052

GAC AGC TTT GCT CTT CCT TCT GGA TGT TAA
E S F A L P S G C

FIG.3D npl: Ala - Asp - Tyr - Gln - Val - Tyr - Ala - Trp - Gly - Ile - Asn - Asp - Pro - (Thr) -
p45: Ala - Thr - Tyr - Lys - Val - Tyr - Pro - Trp - Gly - Val - Asn - Asp - Pro - Ser -

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Ala Xaa Tyr Xaa Val Tyr Xaa Trp Gly Xaa Asn Asp Pro
1               5                   10
```

( 2 ) INFORMATION FOR SEQ ID NO:2:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i ) MOLECULE TYPE: peptide -continued ( x i ) SEQUENCE DESCRIPTION: SEQ ID NO:2:

| | | | | | | | | | | | | | |
|---|---|---|---|---|---|---|---|---|---|---|---|---|---|
| Ala | Thr | Tyr | Lys | Val | Tyr | Pro | Trp | Gly | Val | Asn | Asp | Pro | Ser |
| 1 | | | | 5 | | | | | 10 | | | | |

( 2 ) INFORMATION FOR SEQ ID NO:3:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

| | | | | | | | | | | | | | |
|---|---|---|---|---|---|---|---|---|---|---|---|---|---|
| Ala | Asp | Tyr | Gln | Val | Tyr | Ala | Trp | Gly | Ile | Asn | Asp | Pro | Thr |
| 1 | | | | 5 | | | | | 10 | | | | |

( 2 ) INFORMATION FOR SEQ ID NO:4:

( i ) SEQUENCE CHARACTERISTICS:
( A ) LENGTH: 632 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Arg | Phe | Ser | Asp | Ser | Leu | Leu | Leu | Ile | Gly | Leu | Ser | Ser | Leu | Ala |
| 1 | | | | 5 | | | | | 10 | | | | | 15 | |
| Gly | Ala | His | Pro | Ser | Arg | Arg | Ala | Pro | Asn | Pro | Ser | Pro | Leu | Ser | Lys |
| | | | 20 | | | | | 25 | | | | | 30 | | |
| Arg | Gly | Leu | Asp | Leu | Glu | Ala | Phe | Lys | Leu | Pro | Pro | Met | Ala | Glu | Tyr |
| | | 35 | | | | | 40 | | | | | 45 | | | |
| Val | Pro | Gln | Asp | Glu | Val | Pro | Asp | Asp | Val | Ser | Ala | Lys | Val | Val | Thr |
| | 50 | | | | | 55 | | | | | 60 | | | | |
| Lys | Arg | Ala | Asp | Tyr | Thr | Glu | Thr | Ala | Lys | Asp | Leu | Val | Lys | Ser | Thr |
| 65 | | | | | 70 | | | | | 75 | | | | | 80 |
| Phe | Pro | Lys | Ala | Thr | Phe | Arg | Met | Val | Thr | Asp | His | Tyr | Val | Gly | Ser |
| | | | | 85 | | | | | 90 | | | | | 95 | |
| Asn | Gly | Ile | Ala | His | Val | Asn | Phe | Lys | Gln | Thr | Val | Asn | Gly | Ile | Asp |
| | | | 100 | | | | | 105 | | | | | 110 | | |
| Ile | Asp | Asn | Ala | Asp | Phe | Asn | Val | Asn | Ile | Gly | Ala | Asp | Gly | Glu | Val |
| | | 115 | | | | | 120 | | | | | 125 | | | |
| Phe | Ser | Tyr | Gly | Asn | Ser | Phe | Tyr | Glu | Gly | Lys | Ile | Pro | Gly | Pro | Leu |
| | 130 | | | | | 135 | | | | | 140 | | | | |
| Thr | Lys | Arg | Asp | Glu | Lys | Asp | Pro | Val | Asp | Ala | Leu | Lys | Asp | Thr | Val |
| 145 | | | | | 150 | | | | | 155 | | | | | 160 |
| Asp | Val | Leu | Ser | Leu | Pro | Val | Glu | Ala | Asp | Lys | Ala | Lys | Ala | Glu | Lys |
| | | | | 165 | | | | | 170 | | | | | 175 | |
| Lys | Ser | Lys | Asn | His | Tyr | Thr | Phe | Thr | Gly | Thr | Lys | Gly | Thr | Val | Ser |
| | | | 180 | | | | | 185 | | | | | 190 | | |
| Lys | Pro | Glu | Ala | Lys | Leu | Thr | Tyr | Leu | Val | Asp | Glu | Asn | Lys | Glu | Leu |
| | | 195 | | | | | 200 | | | | | 205 | | | |
| Lys | Leu | Thr | Trp | Arg | Val | Glu | Thr | Asp | Ile | Val | Asp | Asn | Trp | Leu | Leu |
| | 210 | | | | | 215 | | | | | 220 | | | | |
| Thr | Tyr | Val | Asn | Ala | Ala | Lys | Thr | Asp | Glu | Val | Val | Gly | Val | Val | Asp |
| 225 | | | | | 230 | | | | | 235 | | | | | 240 |

-continued

```
Tyr Val Asn Glu Ala Thr Tyr Lys Val Tyr Pro Trp Gly Val Asn Asp
                245                 250                 255

Pro Ser Lys Gly Ser Arg Ser Thr Val Glu Asn Pro Trp Asn Leu Ala
            260                 265                 270

Ala Ser Glu Phe Thr Trp Leu Ser Asp Gly Ser Asn Asn Tyr Thr Thr
        275                 280                 285

Thr Arg Gly Asn Asn Gly Ile Ala Gln Val Asn Pro Ser Gly Gly Ser
    290                 295                 300

Thr Tyr Leu Asn Asn Tyr Arg Pro Asp Ser Pro Ser Leu Lys Phe Glu
305                 310                 315                 320

Tyr Asp Tyr Ser Thr Ser Thr Thr Thr Pro Thr Thr Tyr Arg Asp Ala
                325                 330                 335

Ser Ile Ala Gln Leu Phe Tyr Thr Ala Asn Lys Tyr His Asp Leu Leu
            340                 345                 350

Tyr Leu Leu Gly Phe Thr Glu Gln Ala Gly Asn Phe Gln Thr Asn Asn
        355                 360                 365

Asn Gly Gln Gly Gly Val Gly Asn Asp Met Val Ile Leu Asn Ala Gln
    370                 375                 380

Asp Gly Ser Gly Thr Asn Asn Ala Asn Phe Ala Thr Pro Ala Asp Gly
385                 390                 395                 400

Gln Pro Gly Arg Met Arg Met Tyr Leu Trp Thr Tyr Ser Thr Pro Gln
                405                 410                 415

Arg Asp Cys Ser Phe Asp Ala Gly Val Val Ile His Glu Tyr Thr His
            420                 425                 430

Gly Leu Ser Asn Arg Leu Thr Gly Gly Pro Ala Asn Ser Gly Cys Leu
        435                 440                 445

Pro Gly Gly Glu Ser Gly Gly Met Gly Glu Gly Trp Gly Asp Phe Met
    450                 455                 460

Ala Thr Ala Ile His Ile Gln Ser Lys Asp Thr Arg Ala Ser Asn Lys
465                 470                 475                 480

Val Met Gly Asp Trp Val Tyr Asn Asn Ala Ala Gly Ile Arg Ala Tyr
                485                 490                 495

Pro Tyr Ser Thr Ser Leu Thr Thr Asn Pro Tyr Thr Tyr Lys Ser Val
            500                 505                 510

Asn Ser Leu Ser Gly Val His Ala Ile Gly Thr Tyr Trp Ala Thr Val
        515                 520                 525

Leu Tyr Glu Val Met Trp Asn Leu Ile Asp Lys His Gly Lys Asn Asp
    530                 535                 540

Ala Asp Glu Pro Lys Phe Asn Asn Gly Val Pro Thr Asp Gly Lys Tyr
545                 550                 555                 560

Leu Ala Met Lys Leu Val Val Asp Gly Met Ser Leu Gln Pro Cys Asn
                565                 570                 575

Pro Asn Met Val Gln Ala Arg Asp Ala Ile Ile Asp Ala Asp Thr Ala
            580                 585                 590

Leu Thr Lys Gly Ala Asn Lys Cys Glu Ile Trp Lys Gly Phe Ala Lys
        595                 600                 605

Arg Gly Leu Gly Thr Gly Ala Lys Tyr Ser Ala Ser Ser Arg Thr Glu
    610                 615                 620

Ser Phe Ala Leu Pro Ser Gly Cys
625                 630
```

( 2 ) INFORMATION FOR SEQ ID NO:5:

( i ) SEQUENCE CHARACTERISTICS:

( A ) LENGTH: 2052 base pairs

-continued ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:5:

```
ATGCGTTTCT CCGACTCTCT CCTCCTCATC GGCCTATCCA GCCTCGCTGG TGCTCATCCC    60
AGCAGAAGGG CTCCTAATCC TTCACCGCTG AGCAAGCGTG GCCTCGACCT GGAAGCTTTT   120
AAGCTTCCTC CCATGGCCGA GTACGTTCCT CAGGACGAGG TTCCTGATGA TGTCAGTGCC   180
AAGGTCGTCA CCAAGCGCGC TGATTACACC GAGACTGCCA AGGACTTGGT TAAGTCGACT   240
TTCCCCAAGG CTACTTTCCG TATGGTCACG GATCACTATG TTGGTAGCAA CGGAATTGCG   300
CATGTAAACT TTAAGCAGAC TGTCAACGGT ATTGATATCG ACAATGCTGA TTTCAACGTC   360
AACGTGGGTA TTCTCAAGAC TTTGGGGAGT TTGGAATGTG CTGACATGGA TACAGATTGG   420
CGCTGACGGC GAGGTCTTCT CCTACGGAAA CAGCTTCTAC GAGGGCAAGA TTCCCGGTCC   480
TCTTACCAAG CGTGACGAGA AAGACCCCGT CGACGCTCTC AAGGACACCG TTGATGTTCT   540
TTCTCTCCCC GTTGAGGCTG ACAAGGCCAA GGCTGAGAAG AAGAGCAAGA ACCACTACAC   600
CTTCACTGGT ACCAAGGGTA CCGTCAGCAA GCCCGAGGCT AAGCTCACCT ACCTTGTTGA   660
TGAGAACAAG GAGCTCAAGC TCACATGGAG AGTTGAGACT GATATTGTTG ACAACTGGCT   720
GTTGACTTAT GTCAATGCTG CCAAGACTGA TGAGGTTGTT GGTGTTGTTG ACTACGTCAA   780
TGAGGCGACA TACAAGGTCT AGTACGTATT TCCATAAATT GACGATTGGG AAAGAATTGA   840
CCGTTGTATT ATAGTCCTTG GGGTGTCAAT GATCCCTCCA AGGGATCTCG CTCCACTGTT   900
GAGAACCCCT GGAATCTCGC GGCCTCCGAG TTCACCTGGC TCAGCGACGG CTCAAACAAC   960
TACACCACAA CCCGCGGGAA CAATGGAATT GCACAGGTGA ATCCTTCAGG GGGCTCCACG  1020
TATCTGAACA ATTACCGTCC TGATAGCCCG TCGCTGAAGT TCGAGTATGA TTACTCCACC  1080
AGCACCACTA CACCCACCAC CTACCGCGAT GCTTCCATCG CTCAGCTTTT CTACACAGCC  1140
AACAAGTACC ACGACCTCCT CTACCTTCTT GGCTTTACCG AACAGGCTGG TAACTTCCAG  1200
ACCAACAACA ATGGCCAGGG TGGTGTAGGA AACGATATGG TTATCCTCAA CGCTCAGGAC  1260
GGAAGCGGCA CCAACAACGC CAACTTCGCT ACACCCGCTG ACGGTCAGCC CGGCCGCATG  1320
CGAATGTATC TCTGGACATA CAGCACACCC CAGCGTGACT GCAGTTTCGA CGCTGGCGTT  1380
GTTATCCACG AGTACACTCA CGGTCTCTCC AACCGTCTCA CAGGTGGCCC TGCCAACTCG  1440
GGTTGTCTTC CCGGTGGTGA ATCCGGTGGC ATGGGTGAGG GCTGGGGTGA CTTCATGGCT  1500
ACTGCCATTC ACATCCAATC CAAGGATACC CGCGCTAGCA ACAAGGTCAT GGGTGACTGG  1560
GTGTACAACA ACGCAGCTGG TATCCGAGCT TATCCTTACA GTACAAGCCT TACCACTAAC  1620
CCTTACACTT ACAAGAGTGT TAACAGTCTC AGTGGAGTCC ATGCTATTGG TACTTACTGG  1680
GCTACTGTTC TGTATGAGGT TATGTGGAAC CTCATCGACA AGCATGGGAA GAATGATGCG  1740
GATGAGCCCA AATTCAACAA CGGCGTTCCT ACAGATGGCA AATATCTTGC TATGAAGTTA  1800
GTAGTGGATG GCATGTCGCT GTAAGTTGTC CCTTGGATTT GTAGGAGTTC TTATCTAACG  1860
TTTAATAGGC AACCTTGCAA CCCCAACATG GTCCAGGCCC GAGACGCCAT CATCGACGCC  1920
GACACCGCTC TTACCAAGGG AGCTAACAAG TGCGAGATCT GGAAGGGCTT TGCCAAGCGT  1980
GGTCTTGGAA CTGGTGCCAA GTATAGTGCT TCCAGCCGTA CTGAGAGCTT TGCTCTTCCT  2040
TCTGGATGTT AA                                                      2052
```

( 2 ) INFORMATION FOR SEQ ID NO:6:

( i ) SEQUENCE CHARACTERISTICS:
( A ) LENGTH: 1899 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:6:

```
ATGCGTTTCT CCGACTCTCT CCTCCTCATC GGCCTATCCA GCCTCGCTGG TGCTCATCCC   60
AGCAGAAGGG CTCCTAATCC TTCACCGCTG AGCAAGCGTG GCCTCGACCT GGAAGCTTTT  120
AAGCTTCCTC CCATGGCCGA GTACGTTCCT CAGGACGAGG TTCCTGATGA TGTCAGTGCC  180
AAGGTCGTCA CCAAGCGCGC TGATTACACC GAGACTGCCA AGGACTTGGT TAAGTCGACT  240
TTCCCCAAGG CTACTTTCCG TATGGTCACG GATCACTATG TTGGTAGCAA CGGAATTGCG  300
CATGTAAACT TTAAGCAGAC TGTCAACGGT ATTGATATCG ACAATGCTGA TTTCAACGTC  360
AACATTGGCG CTGACGGCGA GGTCTTCTCC TACGGAAACA GCTTCTACGA GGGCAAGATT  420
CCCGGTCCTC TTACCAAGCG TGACGAGAAA GACCCCGTCG ACGCTCTCAA GGACACCGTT  480
GATGTTCTTT CTCTCCCCGT TGAGGCTGAC AAGGCCAAGG CTGAGAAGAA GAGCAAGAAC  540
CACTACACCT TCACTGGTAC CAAGGGTACC GTCAGCAAGC CCGAGGCTAA GCTCACCTAC  600
CTTGTTGATG AGAACAAGGA GCTCAAGCTC ACATGGAGAG TTGAGACTGA TATTGTTGAC  660
AACTGGCTGT TGACTTATGT CAATGCTGCC AAGACTGATG AGGTTGTTGG TGTTGTTGAC  720
TACGTCAATG AGGCGACATA CAAGGTCTAT CCTTGGGGTG TCAATGATCC CTCCAAGGGA  780
TCTCGCTCCA CTGTTGAGAA CCCCTGGAAT CTCGCGGCCT CCGAGTTCAC CTGGCTCAGC  840
GACGGCTCAA ACAACTACAC CACAACCCGC GGGAACAATG GAATTGCACA GGTGAATCCT  900
TCAGGGGGCT CCACGTATCT GAACAATTAC CGTCCTGATA GCCCGTCGCT GAAGTTCGAG  960
TATGATTACT CCACCAGCAC CACTACACCC ACCACCTACC GCGATGCTTC CATCGCTCAG 1020
CTTTTCTACA CAGCCAACAA GTACCACGAC CTCCTCTACC TTCTTGGCTT TACCGAACAG 1080
GCTGGTAACT TCCAGACCAA CAACAATGGC CAGGGTGGTG TAGGAAACGA TATGGTTATC 1140
CTCAACGCTC AGGACGGAAG CGGCACCAAC AACGCCAACT TCGCTACACC CGCTGACGGT 1200
CAGCCCGGCC GCATGCGAAT GTATCTCTGG ACATACAGCA CACCCCAGCG TGACTGCAGT 1260
TTCGACGCTG GCGTTGTTAT CCACGAGTAC ACTCACGGTC TCTCCAACCG TCTCACAGGT 1320
GGCCCTGCCA ACTCGGGTTG TCTTCCCGGT GGTGAATCCG GTGGCATGGG TGAGGGCTGG 1380
GGTGACTTCA TGGCTACTGC CATTCACATC CAATCCAAGG ATACCCGCGC TAGCAACAAG 1440
GTCATGGGTG ACTGGGTGTA CAACAACGCA GCTGGTATCC GAGCTTATCC TTACAGTACA 1500
AGCCTTACCA CTAACCCTTA CACTTACAAG AGTGTTAACA GTCTCAGTGG AGTCCATGCT 1560
ATTGGTACTT ACTGGGCTAC TGTTCTGTAT GAGGTTATGT GGAACCTCAT CGACAAGCAT 1620
GGGAAGAATG ATGCGGATGA GCCCAAATTC AACAACGGCG TTCCTACAGA TGGCAAATAT 1680
CTTGCTATGA AGTTAGTAGT GGATGGCATG TCGCTGCAAC CTTGCAACCC CAACATGGTC 1740
CAGGCCCGAG ACGCCATCAT CGACGCCGAC ACCGCTCTTA CCAAGGGAGC TAACAAGTGC 1800
GAGATCTGGA AGGGCTTTGC CAAGCGTGGT CTTGGAACTG GTGCCAAGTA TAGTGCTTCC 1860
AGCCGTACTG AGAGCTTTGC TCTTCCTTCT GGATGTTAA                        1899
```

( 2 ) INFORMATION FOR SEQ ID NO:7:

( i ) SEQUENCE CHARACTERISTICS:
( A ) LENGTH: 32 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:7:

```
Thr Ala Tyr Ala Ala Arg Gly Thr Ile Thr Ala Tyr Cys Cys Ile Thr
1               5                   10                  15

Gly Gly Gly Gly Ile Gly Thr Ile Ala Ala Tyr Gly Ala Tyr Cys Cys
            20                  25                  30
```

(2) INFORMATION FOR SEQ ID NO:8:

(i) SEQUENCE CHARACTERISTICS:
(A) LENGTH: 29 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:8:

```
Gly Thr Tyr Gly Gly Ile Gly Gly Ile Thr Thr Arg Gly Gly Ile Thr
1               5                   10                  15

Thr Arg Thr Ala Cys Cys Ala Ile Gly Thr Tyr Cys Gly
            20                  25
```

(2) INFORMATION FOR SEQ ID NO:9:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:9:

```
GGATCCTCGA ATTCTCTTCA GATCTCTTCA CCATGG                          36
```

(2) INFORMATION FOR SEQ ID NO:10:

(i) SEQUENCE CHARACTERISTICS:
(A) LENGTH: 13 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:10:

```
GGATCCACCA TGG                                                   13
```

METALLOPROTEASE HAVING INCREASED ACTIVITY

This application is a divisional application of co-pending application Ser. No. 08/398,489, filed Mar. 3, 1995 which is a continuation-in-part of application Ser. No. 08/238,108, filed on May 4, 1994 incorporated herein by reference.

FIELD OF THE INVENTION

The present invention relates to a novel metalloprotease obtainable from a fungus having increased proteolytic activity as well as isolated nucleic acid fragments encoding said metalloprotease. The invention further relates to vectors, DNA constructs, and recombinant host cells comprising said nucleic acid fragments.

BACKGROUND OF THE INVENTION

Metalloproteases contain a catalytic zinc metal center which participates in the hydrolysis of the peptide backbone (reviewed in Power and Harper, in Protease Inhibitors, A. J. Barrett and G. Salversen (eds.) Elsevier, Amsterdam, 1986, p. 219). The active zinc center differentiates some of these proteases from calpains and trypsins whose activities are dependent upon the presence of calcium. Examples of metalloproteases include carboxypeptidase A, carboxypeptidase B, and thermolysin.

Metalloproteases have been isolated from a number of procaryotic and eucaryotic sources, e.g. *Bacillus subtilis* (McConn et al., 1964, J. Biol. Chem. 239:3706); *Bacillus megaterium;* Serratia (Miyata et al., 1971, Agr. Biol. Chem. 30 35:460); *Clostridium bifermentans* (MacFarlane et al., 1992, App. Environ. Microbiol. 58:1195–1200), *Legionella pneumophila* (Moffat et al., 1994, Infection and Immunity 62:751–3). In particular, acidic metalloproteases have been isolated from broad-banded copperhead venoms (Johnson and Ownby, 1993, Int. J. Biochem. 25:267–278), rattlesnake venoms (Chlou et al., 1992, Biochem. Biophys. Res. Commun. 187:389–396) and articular cartilage (Treadwell et al., 1986, Arch. Biochem. Biophys. 251:715–723). Neutral metalloproteases, specifically those having optimal activity at neutral pH have, for example, been isolated from *Aspergillus sojae* (Sekine, 1973, Agric. Biol. Chem. 37:1945–1952). Neutral metalloproteases obtained from Aspergillus have been classified into two groups, npI and npII (Sekine, 1972, Agric. Biol. Chem. 36:207–216). So far, success in obtaining amino acid sequence information from these fungal neutral metalloproteases has been limited. An npII metalloprotease isolated from *Aspergillus oryzae* has been cloned based on amino acid sequence presented in the literature (Tatsumi et al., 1991, Mol. Gen. Genet. 228:97–103). However, to date, no npI fungal metalloprotease has been cloned or sequenced. Alkaline metalloproteases, for example, have been isolated from *Pseudomonas aeruginosa* (Baumann et al., 1993, EMBO J 12:3357–3364) and the insect pathogen *Xenorhabdus luminescens* (Schmidt et al., 1998, Appl. Environ. Microbiol. 54:2793–2797).

Metalloproteases have been found to have a number of uses. For example, there is strong evidence that a metalloprotease is involved in the in vivo proteolytic processing of the vasoconstrictor, endothelin-1. Rat metalloprotease has been found to be involved in peptide hormone processing. However, there has been no evidence presented in the prior art that metalloproteases could be useful in the in vitro processing of zymogens.

Therefore, it would be advantageous to provide novel metalloproteases with a specific range of substrates. Specifically, it would be useful to produce novel metalloproteases capable of cleaving in vitro the pro sequence from a recombinantly produced proenzyme. It would also be advantageous to isolate novel metalloproteases or produce metalloproteases in high yield so that the metalloproteases could be used in vitro. It would be advantageous to determine the amino acid and/or nucleic acid sequence of these metalloproteases in order to determine, e.g. conserved and nonconserved regions and active sites.

SUMMARY OF THE INVENTION

The present invention relates to a substantially pure metalloprotease obtainable from a fungus having the following characteristics: (a) a mdlecular weight from about 40,000 daltons to about 50,000 daltons as determined by SDS polyacrylamide gel electrophoresis; (b) functions optimally at a pH between about 5.5 and 10.0; (c) is at least about 10 times more effective than a metalloprotease obtainable from Bacillus in converting a proenzyme to an active trypsin-like protease obtainable from a strain of *F. oxysporum* deposited at the Deutsche Sammlung von Mikroorganismen, Gottingen, Germany under the number DSM 2672 under the Budapest Treaty on Jun. 6, 1983 at a pH between about 6.0 and 7.5 at about 25°–30° C. for about 30–60 min.; and (d) is less effective than a metalloprotease obtainable from Bacillus in cleaving the peptide backbone of casein.

In one embodiment, the metalloprotease of the present invention functions optimally at a pH of about 5.5–6.0. In another embodiment, greater than about 50% of the metalloprotease's activity is between about pH 8 and 11. In a specific embodiment, the metalloprotease has a pH optimum of about 9.5. The metalloprotease may also have a temperature optimum of about 50° C.

In another embodiment, the metalloprotease may be about 10 to about 50 times more effective than a metalloprotease, e.g. thermolysin obtainable from Bacillus, e.g., *Bacillus stearothermophilus* and *Bacillus thermoproteolyticus* in cleaving a mercaptopeptide. The effectiveness of a metalloprotease may be determined by comparing the specific activity of one metalloprotease.to another metalloprotease with respect to a specific substrate.

In a specific embodiment, the metalloprotease of the present invention has an N-terminal amino acid sequence depicted in SEQ ID NO:1:

Ala-Xaa-Tyr-Xaa-Val-Tyr-Xaa-Trp-Gly-Xaa-Asn-Asp-Pro

In a most specific embodiment, the metalloprotease of the present invention has an N-terminal amino acid sequence depicted in SEQ ID NOS:2 or 3. In another embodiment, the metalloprotease of the present invention comprises the amino acid sequence depicted in SEQ ID NO:4.

The metalloprotease of the present invention may be obtainable by (a) fermentation of a fungal strain; (b) recovering the supernatant of the fermentation of (a); and (c) isolating the metalloprotease from the supernatant of (b) to obtain the substantially pure metalloprotease.

The invention is also related to an isolated nucleic acid fragment comprising a nucleic acid sequence encoding the metalloprotease of the present invention, described above. In one embodiment, the nucleic acid fragment comprises the nucleic acid sequence depicted in SEQ ID NO:5. In another embodiment, the nucleic acid fragment comprises the nucleic acid sequence depicted in SEQ ID NO:6.

In order to facilitate production of the novel metalloprotease, the invention also provides vectors, DNA constructs and recombinant host cells comprising the claimed nucleic acid fragment, which vectors, DNA construct and recombinant host cells are useful in the recombinant production of the metalloprotease. The nucleic acid fragment may be operably linked to transcription and translation signals capable of directing expression of the metalloprotease in the host cell of choice. Recombinant production of the metalloprotease of the invention is achieved by culturing a host cell transformed or transfected with the nucleic acid fragment of the invention, or progeny thereof, under conditions suitable for expression of the metalloprotease, and recovering the metalloprotease from the culture.

The metalloproteases of the present invention may be used to cleave a pro sequence from a proenzyme resulting in the production of an active or mature enzyme. Furthermore, the metalloproteases of the present invention may be used in a method and/or kit to measure the level of active enzyme activity after cleavage of the pro sequence from said enzyme.

DEFINITIONS

As defined herein "functioning optimally" denotes that the enzyme exhibits significant (i.e. at least about 30% of maximum, preferably at least about 50%, and most preferably from 50% to maximum) activity within the pH range of between about 5.5 and 10.0, as determined by released trypsin activity from protrypsin-like *Fusarium oxysporum* protease obtainable from a strain of *F. oxysporum* deposited at the Deutsche Sammlung von Mikroorganismen, Gottingen, Germany under the number DSM 2672 using the specific substrate N-Benzoyl-L-arginine p-nitroanilide hydrochloride (L-BAPNA). Specifically, the metalloprotease is mixed with the *F. oxysporum* trypsin-like protease incubated for about 30–60 min. at about 25°–30° C. and the amount of trypsin activity is measured using L-BAPNA as a substrate by determining absorption change at 405 nm. The result is calculated relative to the trypsin content of a reference Fusarium trypsin-like protease. Alternatively, the activity of the protease may be determined by standard metalloprotease assays known in the art. For example, protease activity can be detected using a protein substrate such as casein. Specifically, the activity may be quantitated by an in vitro calorimetric assay in which the metalloprotease cleaves succinylated casein. The free primary amino groups created by proteolytic hydrolysis are quantitated calorimetrically. Other substrates include but are not limited to 2,4-dintrophenyl derivatives. The activity may also be quantitated by an in vitro fluorescent assay, when casein contains a fluorescent label, e.g., FTC (fluorescein isothiocyanate).

As defined herein, "less effective" indicates that the metalloprotease hydrolyzes at least 25% less casein than thermolysin, dispase and/or *Bacillus stearothermophilus* neutral metalloprotease after incubation at about 25°–30° C. for about 30–60 minutes at about pH 6.5, using e.g., the procedures disclosed in Example 5.

As defined herein, a "substantially pure" metalloprotease is a metalloprotease which is essentially (i.e. ≧90%) free of other non-metalloprotease proteins.

As defined herein, an "active trypsin-like protease" indicates a form of the enzyme exhibiting enzymatic activity as determined by procedures known in the art.

As defined herein, the term "proenzyme" indicates a precursor or proform of the enzyme. Typically, the proenzyme is constituted by a propeptide part and a polypeptide part comprising the amino acid sequence of the active enzyme. The proenzyme may also be termed a zymogen or a precursor.

As defined herein, the term Ofermentation, indicates any method of cultivation of the cell resulting in the expression or isolation of the metalloprotease. Thus, the fermentation may be understood as comprising shake flask cultivation, small or large scale fermentation (including continuous, batch and fed-batch fermentations) in laboratory or industrial fermentors etc. performed in suitable fermentation media and under conditions allowing the metalloprotease to be expressed or isolated.

BRIEF DESCRIPTION OF THE FIGURES

FIG. 3A–3D shows the genomic DNA sequence and deduced amino acid sequence of p45.

DETAILED DESCRIPTION OF THE INVENTION

Isolation of the Metalloprotease

Figure 1:
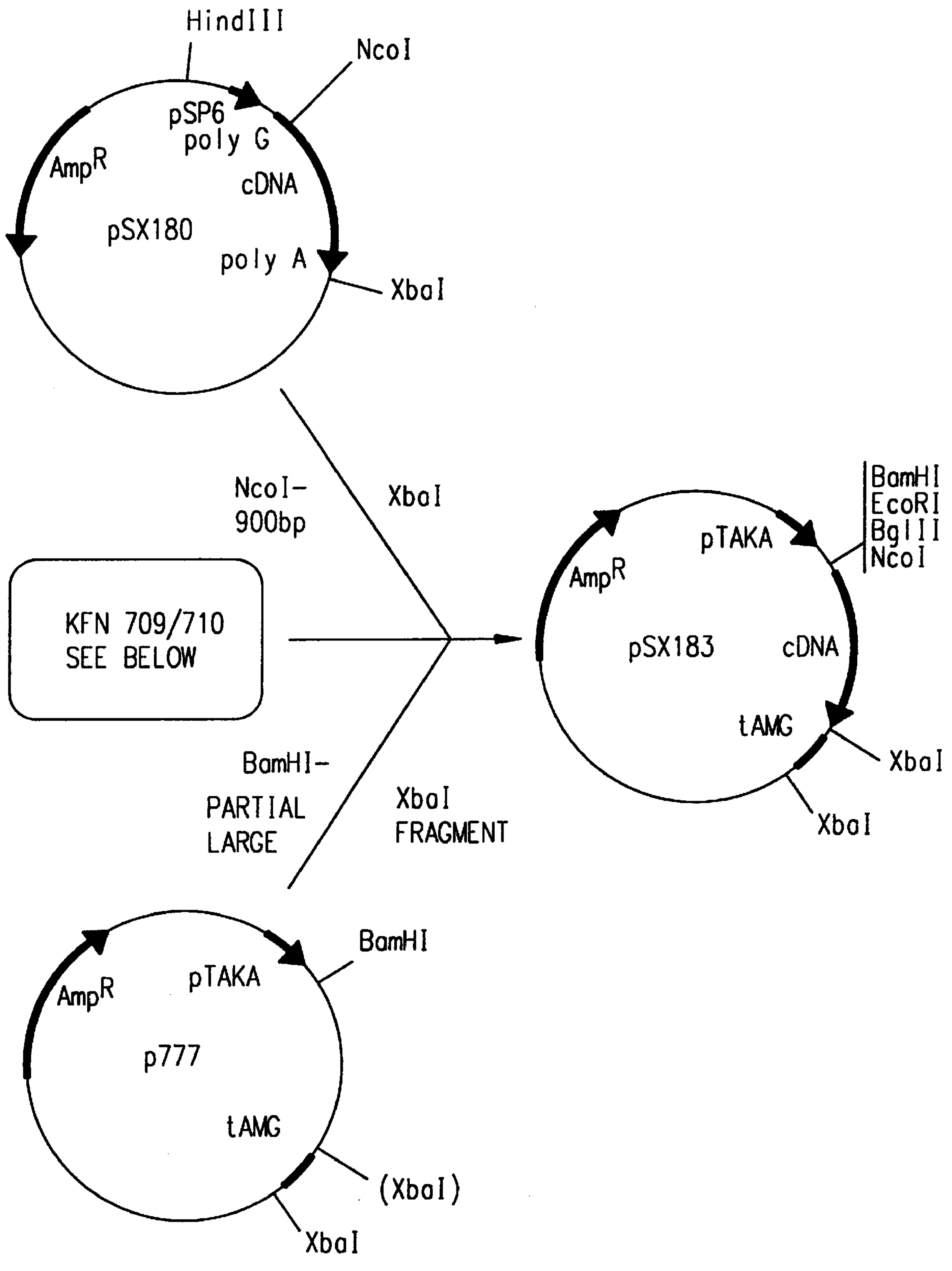
FIG. 1 illustrates the construction of the expression plasmid pSX183 used for the expression of a recombinant trypsin-like *F. oxysporum* protease further described in the accompanying examples.

The metalloprotease of the present invention may be recovered from the supernatant of a fermentation of fungal cells. In one embodiment, the metalloprotease of the present invention is obtainable from the supernatant of a Fusarium fermentation, e.g. *Fusarium oxysporum,* specifically a strain of *F. oxysporum* deposited at the Deutsche Sammlung von Mikroorganismen, Gottingen, Germany under the number DSM 2672. In another embodiment, the metalloprotease of the present invention is obtainable from the supernatant of an Aspergillus fermentation, e.g. a strain of *Aspergillus oryzae, Aspergillus niger,* or *Aspergillus nidulan.*

The fungus may be cultured using procedures known in the art (see, e.g. Bennett, J. W. and LaSure, L. (eds.), More Gene Manipulations in Fungi, Academic Press, Calif., 1991) The metalloprotease of the present invention may be recovered from the medium by centrifugation or filtration, precipitating the proteinaceous components of the supernatant or filtrate by means of a salt, e.g. ammonium sulphate, followed by purification by a variety of chromatographic procedures, e.g. ion exchange chromatography, gel filtration chromatography, affinity chromatography, or the like.

The isolated metalloprotease is characterized by e.g. SDS-PAGE and assayed using procedures known in the art. For example, as described above, the metalloprotease may be assayed for released trypsin activity from the recombinant proform encoded by pro-trypsin-like *Fusarium oxysporum* protease obtainable from a strain of *F. oxysporum* deposited at the Deutsche Sammlung von Mikroorganismen, Gottingen, Germany under the number DSM 2672 using the specific substrate N-Benzoyl-L-arginine p-nitroanilide hydrochloride (L-BAPNA). The activity of the metalloprotease of the present invention may also be assayed by its ability to cleave the primary amino groups from casein.

Cloning and Expression of The Metalloprotease Gene

The nucleic acid sequences encoding the metalloprotease (s) of the present invention as well as the DNA construct of the invention may be of genomic or cDNA origin, for instance obtained by preparing a genomic or cDNA library of an appropriate organism, and screening for nucleic acid sequences coding for all or part of the proenzyme or metalloprotease by hybridization using synthetic oligonucleotide probes, e.g. prepared on the basis of the amino acid sequence of the proenzyme or metalloprotease, in accordance with standard techniques (cf. Sambrook et al., Molecular Cloning: A Laboratory Manual, 2nd Ed., Cold Spring Harbor, 1989).

The nucleic acid sequences and the DNA construct of the invention may also be prepared synthetically by established standard methods, e.g. the phosphoamidite method described by S. L. Beaucage et al. (1981), Tetrahedron Letters 22, pp. 1859–1869 and Matthes et al. (1984), The EMBO J. 3: 801–805. According to the phosphoamidite method, oligonucleotides are synthesized, e.g. in an automatic DNA synthesizer, purified, ligated, and cloned in an appropriate vector.

Finally, the nucleic acid sequences and the DNA construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire DNA construct, in accordance with standard techniques.

The cell used for the expression of the metalloprotease of the present invention in the processes of the invention is suitably a cell which, on cultivation, produces large amounts of the metalloprotease of the invention. As stated above, the cell may be one which in nature produces the metalloprotease of the invention, but is preferably a cell of the invention which has been transformed with a nucleic acid sequence encoding the metalloprotease. The cell may conveniently be one which has previously been used as a host for producing recombinant proteins, either a prokaryotic or eukaryotic cell, including but not limited to mammalian cells, insect cells, plant cells or fungal cells and is preferably a microorganism such as a bacterium or a fungus. The term "fungus" is intended to comprise filamentous fungi as well as yeasts.

Examples of suitable bacteria are gram positive bacteria of the genus Bacillus such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus megaterium, Bacillus circulans, Bacillus lautus* and of the genus Streptomyces such as *Streptomyces lividans.* Examples of suitable gram-negative bacteria comprises bacteria of the genus Escherichia such as *E. coli.* The transformation of the bacterial host cell may for instance be effected by protoplast transformation or by using competent cells in a manner known per se. Another suitable bacterial cell is a cell of a Pseudomonas spp. such as *Pseudoimonas cepacia, Pseudomonas fragi, Pseudomonas gladioli, Pseudomonas fluorescens, Pseudomonas stutzeri, Pseudomonas alcaligenes, Pseudomonas pseudoalcaligenes, Pseudomonas putida, Pseudomonas glumae* or *Pseudomonas aeruginosa.*

Alternatively, the cell may be a fungus, i.e. a cell of a yeast or of a filamentous fungus. The yeast cell may, for instance, be a cell of the genus Saccharomyces such as *S. cerevisiae.* The filamentous fungus host organism may, for instance, be a strain of *Aspergillus sp.,* such as *A. niger, A. nidulans* or *A. oryzae.* The techniques used to transform an Aspergillus host cell and obtain expression of the recombinant protein may suitably be as described in EP 238 023. Alternatively, the fungal host cell may be a strain of a *Fusarium sp.*such as *F. oxysporum,* the transformation of which, e.g., may be carried out as described by Malardier et al., 1989, Gene 78: 147–156.

In order to obtain expression, the nucleic acid sequence encoding the metalloprotease is normally preceded by a promoter. The promoter may be any nucleic acid sequence exhibiting a strong transcriptional activity in the host cell of choice and may be derived from a gene encoding an extracellular or intracellular protein such as an amylase, a glucoamylase, a protease, a lipase, a cellulase or a glycolytic enzyme. Examples of suitable promoters, especially when using a bacterial host, are the promoter of the lac operon of *E. coli,* the *Streptomyces coelicolor* agarase gene dagA promoters, the promoters of the *Bacillus licheniformis* $\alpha$ the promoters of the *Bacillus licheniformis* $\alpha$-amylase gene (amyL), the promoters of the *Bacillus stearothermophilus* maltogenic amylase gene (amyM), the promoters of the *Bacillus amyloliquefaciens* $\alpha$-amylase (amyQ), or the promoters of the *Bacillus subtilis* xylA and xinB genes. In a yeast host, a useful promoter is the eno-1 promoter. For transcription in a fungal host, examples of useful promoters are those derived from the gene encoding *A. oryzae* TAKA amylase, *Rhizomucor miehei* aspartic proteinase, *A. niger* neutral $\alpha$-amylase, *A. niger* acid stable $\alpha$-amylase, *A. niger* or *A. awamsii* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters.

Other sequences involved in expression of the metalloprotease include termination and polyadenylation sequences as well as ribosome binding sites and may suitably be derived from the same sources as the promoter. The vector may further comprise a nucleic acid sequence enabling the vector to replicate in the host cell in question, e.g. a suitable origin of replication.

The vector may also comprise a selectable marker, e.g. a gene the product of which complements a defect in the host cell, such as the dal genes from *B.subtilis* or *B.licheniformis,* or one which confers antibiotic resistance such as ampicillin, kanamycin, chloramphenicol or tetracycline resistance. Examples of Aspergillus selection markers include amds, pyrG, argb, niad and sC, a marker giving rise to hygromycin resistance. Preferred for use in an Aspergillus host cell are the amds and pyrG markers of *A. nidulans* or *A. oryzae.* A frequently used mammalian marker is the dihydrofolate reductase (DHFR) gene. Furthermore, selection may be accomplished by co-transformation, e.g. as described in WO 91/17243.

The procedures used to ligate the DNA construct of the invention, the promoter, terminator and other elements, respectively, and to insert them into suitable vectors containing the information necessary for replication, are well known to persons skilled in the art (cf., for instance, Sambrook et al., Molecular Cloning, Cold Spring Harbor, N.Y., 1989).

The cell of the invention either comprising a DNA construct or an expression vector of the invention as defined above is advantageously used as a host cell in the recombinant production of a enzyme of the invention. The host cell may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into. the host chromosome may be performed according to conventional methods, e.g. by homologous or heterologous recombination. Alternatively, the cell may be transformed with an expression vector as described above in connection with the different types of host cells.

The broth or medium used in the processes of the invention for fermentation of the resulting recombinant host cell may be any conventional medium suitable for growing the cell in question. Suitable media, e.g. minimal or complex media, are avaiable from commercial suppliers or may be prepared according to published recipes (e.g. in catalogs of the American Type Culture Collection).

The metalloprotease of the invention may be recovered from the broth by conventional procedures including but not limited to separating the cells from broth by centrifugation or filtration, if necessary, after disruption of the cells, precipitating the proteinaceous components of the supernatant or filtrate by means of a salt, e.g. ammonium sulphate, followed by purification by a variety of chromatographic procedures, e.g. ion exchange chromatography, affinity chromatography, or the like, the actual recovery method being dependant on the kind of enzyme in question.

Those skilled in the art will recognize that the invention is not limited to use of the nucleic acid fragments specifically disclosed herein, for example, in FIG. 3. It will be apparent that the invention also encompasses those nucleotide sequences that encode the same amino acid sequences as depicted in FIG. 3, but which differ from those specifically depicted nucleotide sequences by virtue of the degeneracy of the genetic code. The invention specifically encompasses any variant nucleotide sequence, and the protein encoded thereby,, which protein retains at least about an 80%, preferably 90%, and most preferably 95% homology or identity with one or the other of the amino acid sequences depicted in FIG. 3 and retains metalloprotease and pH optimum activity of the sequences described herein. In particular, variants which retain a high level (i.e., ≧80%) of homology at highly conserved regions of said metalloprotease are contemplated. Furthermore, the invention encompasses any variant that hybridizes to the nucleotide sequence of the metalloprotease under the following conditions:presoaking in 5X SSC and prehydbridizing for 1 hr. at about 40° C. in a solution of 20% formamide, 5X Denhardt's solution, 50 mM sodium phosphate, pH 6.8, and 50 ug denatured sonicated calf thymus DNA, followed by hybridization in the same solution supplemented with 100 uM ATP for 18 hrs. at about 40° C., followed by a wash in 0.4X SSC at a temperature of about 45° C.

Useful variants within the categories defined above include, for example, ones in which conservative amino acid substitutions have been made, which substitutions do not significantly affect the activity of the protein. By conservative substitution is meant that amino acids of the same class may be substituted by any other of that class. For example, the nonpolar aliphatic residues Ala, Val, Leu, and Ile may be interchanges, as may be the basic residues Lys and Arg, or the acidic residues Asp and Glu. Similarly, Ser and Thr are conservative substitutions for each other, as are Asn and Gln. It will be apparent to the skilled artisan that such substitutions can be made outside the regions critical to the function of the molecule and still result in an active enzyme. Retention of the desired activity can readily be determined by using the assay procedures described above.

Uses

The metalloproteases of the present invention are useful in a number of different processes. For example, the metalloproteases of the present invention may be used to cleave a pro sequence from a proenzyme resulting in the production of an active or mature enzyme.

From the above disclosure, it will be apparent that the metalloprotease(s) may be added as such to the fermentation broth in which the cell producing the proenzyme to be converted is cultured. The metalloprotease may be added batchwise or continuously.

Alternatively, the presence of the metalloprotease(s) in the fermentation broth may be accomplished by constructing a cell capable of expressing the proenzyme and the metalloprotease(s), and cultivating the cell under conditions conducive to the production of the proenzyme and metalloprotease metalloprotease(s) and to the subsequent activation of the proenzyme by the metalloprotease(s). A suitable cell may be constructed by being transformed with nucleic acid sequences encoding the proenzyme and metalloprotease metalloprotease(s), optionally present on one or more expression vectors. Alternatively, one may choose a cell already comprising a heterologous nucleic acid fragment containing a nucleic acid sequence encoding, for instance, the proenzyme and inserting a nucleic acid sequence encoding a metalloprotease into said cell (or vice versa) by recombinant DNA methods.

Alternatively, a cell expressing the proenzyme and a cell expressing a metalloprotease capable of converting the proenzyme into an active form may be subjected to co-expression under suitable conditions allowing the expression of said proenzyme and said metalloprotease and the conversion of the proenzyme into an active enzyme. The active enzyme is recovered from the culture. According to this embodiment it is preferred that at least one of said proenzyme and metalloprotease is recombinant.

The metalloproteases of the present invention may be used to in a method and/or kit for determining the amount of activatable proenzyme present in a sample. Such a method comprises (a) incubating the metalloprotease of the present invention and the proenzyme at room temperature for about 30 minutes to about 1 hour; (b) adding a substrate for activated proenzyme to mixture (a); and c) determining the amount of substrate added in step (b) that is cleaved. In a specific embodiment, the proenzyme is a recombinant form of a trypsin-like protease, e.g. from *Fusarium oxysporum*. The substrate may be selected from the group consisting of 2,4-dinitrophenyl derivatives, paranitrophenol derivatized substrates for trypsin, casein or L-BAPNA. In a preferred embodiment, the cleaved substrate can be detected by visible spectroscopy by, for example, determining increase in absorbance of samples at various intervals (e.g. 0.5 min. at 405). The kit may comprise (a) the metalloprotease of the present invention and (b) a substrate for activated proenzyme. The kit of the invention may also comprise a buffer(s).

EXAMPLES

Example 1: Isolation and Characterization of the p45 Metalloprotease from *Fusarium oxysporum*

Materials and Methods:

Purification:

*F. oxysporum* broth is centrifuged at 9000 rpm for 10 min. and the supernatant is filtered through a 0.45 $\mu$m filter. 200 ml of filtrate is concentrated down to 10 ml on an Amicon cell (PM 10 membrane) and Centriprep-0 (Amicon). 5 ml of concentrate is diluted to 100 ml and pH adjusted to 5 with acetic acid and run on a 1 ml MonoS column in the following buffer:0.1M borate, 10 mM DMG, 2 mM calcium chloride, pH 5.2 in a gradient of 0->0.5M sodium chloride over 70 min., after 10 min. of wash in the above-identified buffer at a flow rate of 1 ml/min; 1.5 ml fractions are collected and concentrated on Centricon-10 (Amicon).

Gel filtration using Superose12 (HR 10/30, Pharmacia) is performed in 0.1M borate, 10 mM DMG, 2 mM $CaCl_2$, pH 6.5, flow rate: 0.4 ml/min; 0.4 ml fractions are collected; 200 $\mu$l samples are injected.

Proteolytic enzyme assay:

Metalloprotease activity is measured as released trypsin activity from pro-trypsin-like *Fusarium oxysporum* protease deposited at the Deutsche Sammlung von Mikroorganismen, Gottingen, Germany under the number DSM 2672, after a 30–60 min pre-incubation at 25° C. in 0.1M Tris, 2 mM $CaCl_2$, pH 7 (at lower pH, 100 mM borate, 10 mM DMG, 2 mM $CaCl_2$ is used). The tryptic activity is measured in microtiter plates; 100 $\mu$l samples are mixed with 100 $\mu$l of substrate (Stock: 87 mg/ml L-BAPNA (Sigma) in DMSO, diluted 50-fold in buffer) and the absorption at 405 nm is measured using a Thermomax microplate reader from Molecular Devices.

SDS-PAGE and electroblotting onto PVDF:

SDS-PAGE (10–27%, Novex) is run according to the manufacturer's instructions; samples to be run are preincubated with PMSF before adding sample buffer. Electroblotting onto pro-blot membranes (Applied Biosystems) is performed in 3 mM $Na_2CO_3$, 10 mM $NaHCO_3$, 20% MeOH, pH 9.9 at 30 V for 2 hours using the blotting module from Novex. The pro-blot is stained as described by Applied Biosystems.

IEF-overlay:

Isoelectric focusing (IEF) (Ampholine PAG-plate: pH 3.5–9.5, Pharmacia) is run and stained according to the manufacturer's instructions. The gel to be overlaid is first equilibrated for 15 min in 0.1M Tris, 2 mM $CaCl_2$, pH 8.1 and then overlaid with 10 ml 1% agarose, 0.1M Tris, 2 mM $CaCl_2$, pH 8.1 added 300 1 L-BAPNA stock and 500 Al recombinant pro-trypsin-like *Fusarium oxysporum* protease disclosed, supra (~0.25 mg/ml).

Amino acid analysis and amino acid sequencing:

Microwave facilitated vapor phase hydrolysis of lyophilized samples is performed using the MDS-2000 hydrolysis-station (CEM). 6N HCl containing 1% phenol (scavenger) is used for creating the vapor phase. Hydrolysis time is 20 min at 70 psi (~148° C.). Hydrolyzed samples are lyophilized and redissolved in 20 $\mu$l of 500 pmol/$\mu$l sarcosine and norvaline as internal standard. The analysis is done using the AminoQuant from Hewlett-Packard according to manufacturer's instructions; 1 $\mu$l of sample is injected. Amino acid sequencing is performed using the 476A Protein Sequencer from Applied Biosystems according to manufacturer's instructions; premixed buffers are used for the online-HPLC.

Construction of a recombinant *A. oryzae* strain capable of expressing the trypsin-like *F. oxysporum* protease cDNA encoding a proenzyme form of the trypsin-like *F. oxysporum* protease and having the DNA sequence shown in the appended SEQ ID NO:6 is inserted into the vector pCDV1-PL described by Noma et al. (1986), Nature 319: 640–646 resulting in the plasmid pSX180. The coding region of the CDNA is inserted as a NcoI-XbaI fragment i[ ]nto the Aspergillus expression plasmid p777 (EP 0 489 718) which is cut with BamHI and partially with XbaI. To join the 5' end of the cloned DNA to the vector a synthetic linker DNA KFN709/710 (illustrated in FIG. 1) is added to the ligation reaction. The resulting plasmid pSX183 is co-transformed into *A. oryzae* (IFO 4177) together with plasmid pToC90 carrying the amdS from *A. nidulans* (WO 91/17243). Transformants are selected for growth on acetamide.

Results

Purification of p45 from *F. oxysporum* Broth

The p45 metalloprotease is purified from concentrated and filtered fermentation broth, by using cation-exchange chromatography (MonoS) followed by gel filtration on Superose12. Fractions from MonoS are selected by assaying for metalloprotease activity as released trypsin-like activity from pro-trypsin-like *Fusarium oxysporum* protease disclosed, supra. Metalloprotease containing fractions from the Superose12 column are identified by using the same assay procedure as for the MonoS-fractions. The purified metalloprotease appears as a single band on SDS-PAGE at 45 kDa. Two isoforms of the metalloprotease are observed in IEF (pH 3.5–9.5) at respectively pI 8.4 and 8.7.

Results from amino acid analysis indicate that this metalloprotease (p45) has the N-terminal amino acid sequence shown in the Sequence Listing as SEQ ID NO:2.

Purified *F. oxyoporum* p45 Metalloprotease demonstrates a high specific activity.

Figure 2:
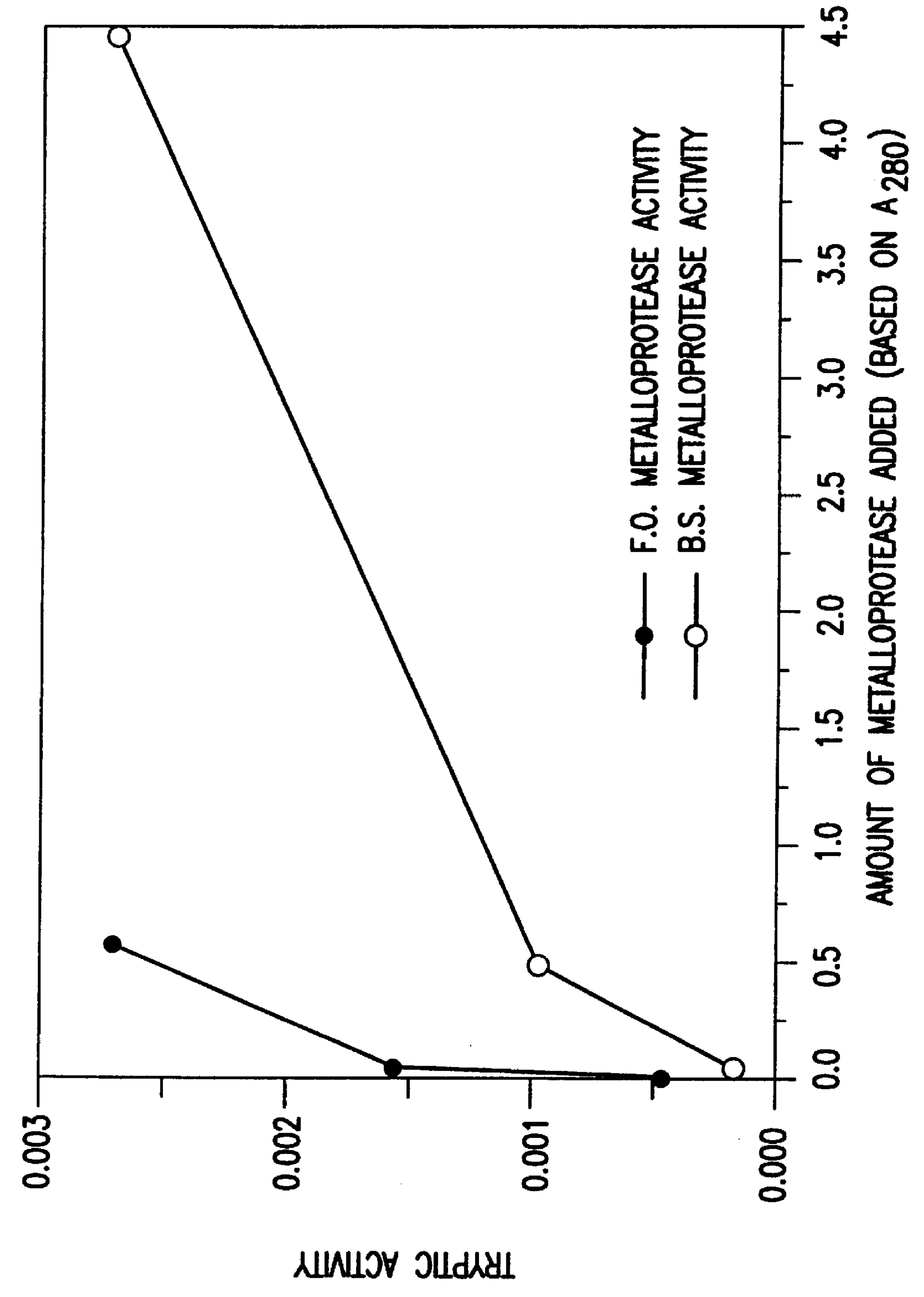
FIG. 2 shows a comparison of *F. oxysporum* proteolytic enzyme activity with that of Bacillus metalloprotease used to process pro *F. oxysporum* protease.

The desired metalloprotease fractions from the gel filtration column are pooled and loaded onto a preparative IEF apparatus. Samples are run at 1000V for 1 hour after the amperage had stabilized and then at 500V for another 30 minutes before 30 fractions of 3 ml each are collected. Only one fraction contained the metalloprotease as seen on SDS-PAGE. The specific activity based, on absorbance of samples at 280 nm, of the Fusarium metalloprotease taken from this fraction appears to be about 10-fold greater than that of the conventional Bacillus metalloprotease used to mature pro-trypsin-like *Fusarium oxysporum* protease disclosed, supra, (FIG. 2).

The p45 is a metalloprotease.

Metalloproteases contain a catalytic zinc metal center which participates in the hydrolysis of the peptide backbone.

The active zinc center differentiates these proteases from calpains whose activities are dependent upon the presence of calcium. Confirmation of a protease as a metallo-protease is loss of proteolytic activity accomplished by removal of the zinc center with 1,10-phenanthroline (1 mM) followed by titration with $Zn^{2+}$ (0.1–100 $\mu$M) to restore full activity.

Table 1 demonstrates that the trypsin-like *Fusarium oxysporum* protease disclosed in the Materials and Methods section of Example 1, supra is not inhibited by 1,10-phenanthroline since similar tryptic activities result with or without inhibitor addition, $33.8\times10^{-4}$ and $34.0\times10^{-4}$ ΔAbs/min respectively. Pro-trypsin-like *Fusarium oxysporum* protease disclosed, supra or *Fusarium oxysporum* metalloprotease samples alone do not contain any tryptic activity (Table 1). However, when combined the metalloprotease cleaves recombinant pro-trypsin-like *Fusarium oxysporum* protease disclosed, supra to yield the active tryptic protease. Metalloprotease activity is halted upon the addition of 1 mM 1,10-phenanthroline (Table 1). However, full reactivation of the Fusarium metalloprotease occurs upon addition of 1 mM $Zn^{2+}$. Analogous results occur when EDTA (1 mM) is substituted for 1,10-phenanthroline.

TABLE 1

Inhibition of Fusarium Metalloprotease with 1,10 Phenanthroline

| Protein | 1,10-phenanthroline (1 mM) | $Zn^{2+}$ (1 mM) | Tryptic Activity ($\Delta$ Abs/min × $10^{-4}$) |
|---|---|---|---|
| Typsin-like *F. oxysporum* protease | – | – | 34.0 |
| Trypsin-like *F. oxysporum* protease | + | – | 33.8 |
| Pro-trypsin-like-*F. oxysporum* protease | – | – | 1.26 |
| p45 Maturase | – | – | 1.33 |
| Pro-trypsin-like *F. oxysporum* protease + p45 Maturase | – | – | 54.0 |
| Pro-trypsin-like *F. oxysporum* protease + p45 Maturase | + | – | 2.9 |
| Pro-trypsin-like *F. oxysporum* protease + p45 Maturase | + | + | 50.6 |

Example 2: Cloning of the *Fusarium oxysporum* p45 Gene

A portion of the *F. oxysporum* p45 gene is first cloned by PCR. One primer is designed using the N-terminal protein sequence (SEQ ID NO:7) and a reverse primer is designed from an internal metalloprotease peptide sequence (SEQ ID NO:8). PCR is performed using the DNA primers and genomic DNA isolated from *Fusarium oxysporum.* Genomic DNA is isolated as follows. Approximately 15 g wet weight *F. oxysporum* is grown in MY50 medium (50 g/l maltodextrin, 2 g/l $Mg_2SO_4$, 10 g/l $KH_2PO_4$, 2 g/l citric acid, 10 g/l yeast extract, 2 g/l urea, 2 g/l $K_2SO_4$, 0.5 ml trace metal solution to pH=6 with 5N NaOH) at 30° C. Mycelia are suspended in 16 ml TE (10 mM Tris-HCl, 1 mM EDTA pH=8.0), split into two tubes, and ca. 12 g of 0.45–0.52 mm glass beads (Thomas Scientific) are added to each tube. The samples are alternately vortexed and iced for 30 second intervals until a noticeable viscosity breakdown occurs. The samples are vortexed two additional 30 second intervals. 2.5 ml 20% SDS is added to each sample. The samples are mixed by inversion, incubated 10 minutes at room temperature, and mixed again. Samples are spun 8 minutes at 3.5 K, room temperature. Supernatants are combined in a 50 ml polypropylene tube. The sample is extracted with an equal volume of TE equilibrated with phenol:chloroform:isoamyl alcohol (25:24:1) then centrifuged 10 minutes at 10,000 rpm, 4° C. The supernatant is treated with 300 $\mu$l 10 mg/ml proteinase K for 30 minutes at 25° C. The DNA is phenol/chloroform /isoamyl alcohol (P/C/I) extracted as described above, ethanol precipitated and dissolved in 5 ml TE. The sample is treated with 150 $\mu$l 10 mg/l RNAase A for 15 minutes at 65° C., then 15 minutes at 25° C. The sample is treated again with proteinase K (100 $\mu$l 10 mg/ml for 1.5 hours at 25° C.) and then P/C/I extracted twice and ethanol precipitated. The DNA is spooled onto a bent pasteur pipet and transferred to 5 ml 80% ethanol. The sample is spun 3 minutes at 10,000 rpm. The DNA pellet is dried briefly, then dissolved in 1 ml TE.

PCR is used to clone a portion of the *F. oxysporum* p45 gene as follows: 50–100 ng *F. oxysporum* genomic DNA is mixed with ca. 100 pmoles each of the synthetic PCR primer DNAs in 1X Taq buffer (Boehringer Mannheim) and a concentration of 100 $\mu$M each of dGTP, DATP, dTTP, and dCTP, in a volume of 50 $\mu$l. Taq DNA polymerase (Boehringer Mannheim), 1–5 units, is added and the PCR incubations are, 95° C. 5 min then 35 cycles of [95° C. 30 seconds: 50° C. 1 minute: 72° C. 1 min]. The PCR reaction produces two DNA fragments of ca. 1.0 and 1.3 kb in length. These fragments are isolated by gel electrophoresis, purified, cloned into an *E. coli* replicating plasmid, and sequenced using standard methods known in the art of molecular biology. The 1.0 kb DNA fragment is found to contain *F. oxysporum* p45 gene sequences by a comparison of the translations of the DNA with the amino acid sequences obtained from the direct protein sequencing. Therefore, this 1.0 kb PCR generated DNA fragment is used as a probe to clone the entire metalloprotease gene from a *F. oxysporum* genomic DNA library.

A genomic DNA library in lambda phage is prepared from the *F. oxysporum* genomic DNA using methods such as those described found in Sambrook et al., 1989, Molecular Cloning: A Laboratory Manual, Cold Spring Harbor, N.Y. A total of 50 $\mu$g genomic DNA is digested in a volume of 200 $\mu$l containing 10 mM Tris, pH 7.5, 50 mM NaCl, 7 MM $MgCl_2$, 7 mM 2-mercaptoethanol, and 4 units restriction enzyme Sau3A for one minute at 25° C. Partially digested DNA of molecular size 10–20 kb is isolated by agarose gel electrophoresis, followed by electroelution into dialysis membrane and concentration using an Elutip-D column (Schleicher and Schuell). One $\mu$g of lambda arms of phage of EMBL4 that had been cut with restriction enzyme BamH1 and treated with phosphatase (Clonetech) is ligated with 300–400 $\mu$g Sau3A cut genomic DNA in a volume of 25 $\mu$l under standard conditions (see Sambrook et al., 1989, Molecular Cloning: A Laboratory Manual, Cold Spring Harbor, N.Y.). Lambda phage are prepared from this ligation mix using a commercially available kit (Gigapack Gold II, Stratagene) following the manufacturer's directions. The plating of ca. 18,000 recombinant lambda phage and the production of filter lifts (to N+ filters, Amersham) were performed using standard methods (Sambrook et al., 1989, Molecular Cloning: A Laboratory Manual, Cold Spring Harbor, N.Y.). The filters are processed for hybridization with a Genius Kit for non-radioactive nucleiic acids detection (Boehringer Mannheim) using the instructions provided by the manufacturer. The DNA used as a p45 probe is the 1.0 kb PCR fragment described above. The probe is labelled by PCR incorporation of dioxigenin (DIG) using a DIG labelling kit and the instructions supplied by the manufacturer. Fifteen ng of the 1.0 kb p45 fragment is mixed in 1X Taq Buffer (Boehringer Mannheim), 1X DIG labelling mix (Boehringer Mannheim) with 100 pmoles each N-terminal primer (SEQ ID NO:7) and internal reverse primer (SEQ ID NO:8), and 1–5 units Taq polymerase (Boehringer Mannheim) in a total volume of 80 $\mu$l. Reaction conditions were: 95° C. 3 minutes, 35×[95° C., 30 seconds; 50° C. 1 minute; 72° C., 1 minute], 72° C., 5 minutes. The filter hybridizations using the DIG labelled probe, and the wash conditions were performed using the instructions provided by the Genius Kit manufacturer.

Hybridizing phage are detected with an alkaline phosphatase-conjugated anti-digoxigenin antibody visualized with Lumiphos 530 as described by the manufacturer (Boehringer Mannheim). DNA preparations are made from the positive lambda clones using the Qiagen Lambda Midi Kit (QIAGEN,Inc.). DNA from one preparation is digested with restriction enzyme EcoRI and a 6.3 kb fragment is subcloned into plasmid pUC118. DNA sequence analysis of portions of this subclone identified the entire coding region of the p45 gene (see FIG. 3 and SEQ ID NO:4).

Total RNA and Poly-A RNA is prepared from *F. oxysporum* according to previous published protocols (Chirgwin et al. Biochemistry 18:5294–5299 (1989), Aviv and Leder, Proc. Natl. Acad. Sci., USA 69:1408–1412 (1972), Sambrook et al., 1989, Molecular Cloning: A Laboratory Manual, Cold Spring Harbor, N.Y.) with the following modifications. Specifically, mycelia is ground in liquid nitrogen to a fine powder and then resuspended, with stirring, in a lysis buffer containing 4M guanidinium thiocyanate, 0.5 % Na-laurylsarcosine, 25 mM Na-citrate, and 0.1M 2-mercaptoethanol, pH=7.0, for 30 minutes at room temperature. Cell debris is removed by low speed (5000 rpm for 30 minutes) centrifugation. Typically, the poly-A RNA fraction is isolated using oligo(dT) cellulose obtained from Boehringer Mannheim.

The polyA RNA is used to generate cDNA using the hairpin/RNaseH method (Sambrook et al., 1989, Molecular Cloning: A Laboratory Manual, Cold Spring Harbor, N.Y.). Specifically, 5 $\mu$g polyA RNA in 5 $\mu$l water is heated at 70° C. then placed on ice. A total reaction mix of 50 $\mu$l is prepared containing the polyA RNA, 50 mM Tris(pH=8.3), 75 mM KCl, 3 mM $MgCl_2$, 10 mM DTT, 1 mM each dGTP DATP dTTP and dCTP, 40 units RNasin 10 $\mu$g oligo (dT12–18) primer, and 1000 units SuperScript II RNase H-reverse transcriptase (Bethesda Research Laboratories). The mix is incubated at 45° C. for one hour. Then 30 $\mu$l of 10 mM Tris, pH 7.5, 1 mM EDTA, 40 $\mu$g glycogen carrier (Boehringer Mannheim), 0.2 volumes 10M ammonium acetate, and 2.5 volumes ethanol were added to precipitate the nucleic acids. After centrifugation, the pellet is resuspended in 20 mM Tris (pH 7.4), 90 mM KCl, 4.6 mM $MgCl_2$, 10 mM ammonium sulphate, 16 $\mu$M βNAD+, 100 $\mu$M each dGTP dATP dTTP dCTP, 44 units *E. coli* DNA polymerase I, 6.25 units RNaseH, and 10.5 units DNA ligase. Second strand DNA synthesis is performed in this solution at 16° C. for 3 hours. The DNA is concentrated by ethanol precipitation and the pellet is resuspended in 30 $\mu$l of 30 mM Na-acetate (pH 4.6), 300 mM NaCl, 1 mM $ZnSO_4$, 0.35 mM DTT, 2% glycerol, and 30 units Mung Bean nuclease (Bethesda Research Laboratories) at 30° C. for 30 minutes. The DNA solution is neutralized with 70 $\mu$l 10 mM Tris, pH 7.5 1 mM EDTA, phenol extracted, and ethanol precipitated. The pellet is treated with 7.5 units T4 polymerase (Invitrogen) at 25° C. for 15 minutes in 50 $\mu$l buffer (20 mM Tris-acetate, pH 7.9, 10 mM Mg-acetate, 50 mM K-acetate, 1 mM DTT, 0.5 mM each dGTP dATP dTTP dCTP). The reaction is stopped by addition of EDTA to 20 mM followed by phenol extraction and ethanol precipitation. The result of this procedure is double stranded cDNA with blunt ends suitable for attachment of DNA linkers and cloning into any vector.

The cDNA with EcoR1 linkers is size fractionated on an agarose gel to obtain cDNAs of molecular size 0.7 kb or greater. The CDNA is recovered from the gel by electroelution and purified by phenol extraction and ethanol precipitation. The size fractionated cDNA is used to construct a lambda cDNA library. The CDNA is cloned into lambda ZIPLOX arms (Gibco BRL). Full length cDNA lambda clones are identified using a 467 bp digoxigenin labeled fragment as probe (bp 336–803 of the genomic clone) with the techniques of plaque lifts and DNA hybridizations as previously described. Full length cDNA is recovered in plasmid pZL1 as described by the manufacturer (strains and plasmid from gibco BRL). The full length cDNA is sequenced and compared with the sequence of the genomic DNA (SEQ ID NO:5). The genomic DNA is 2052 bp in length and contains three introns. The predicted coding region of prepro-p45 metalloprotease consists of a putative 18 amino acid signal sequence, a 226 amino acid pro-region, and a 388 amino acid mature region is shown in SEQ ID NO:6 and in FIG. 3.

Example 3: Coexpression of Both p45 Proteolytic Enzyme and the Trypsin-Like Protease in the Same Microorganism Host (*A. oryzae*)

Figure 4:
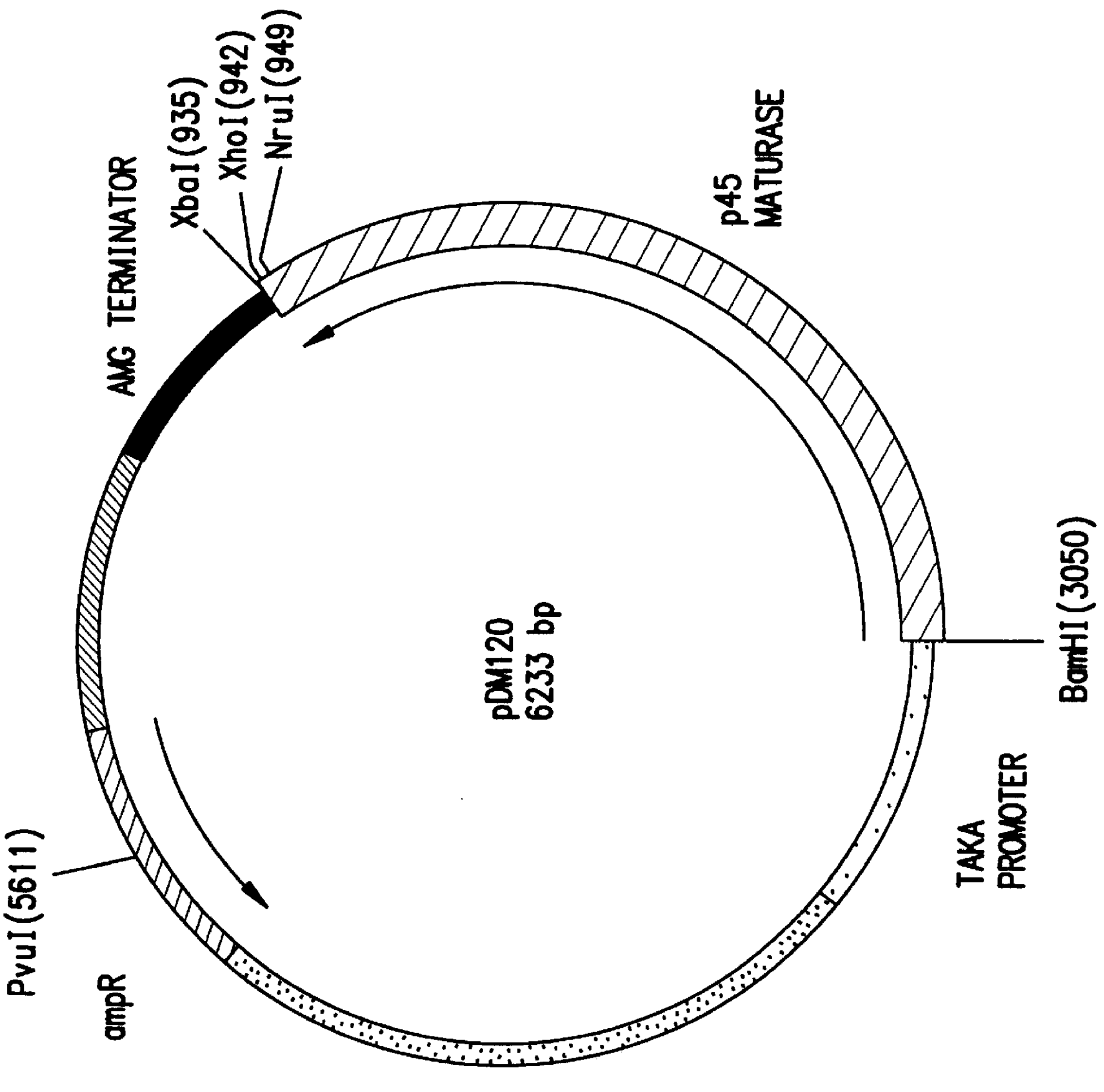
FIG. 4 shows a map of plasmid pDM120.
Figure 5:
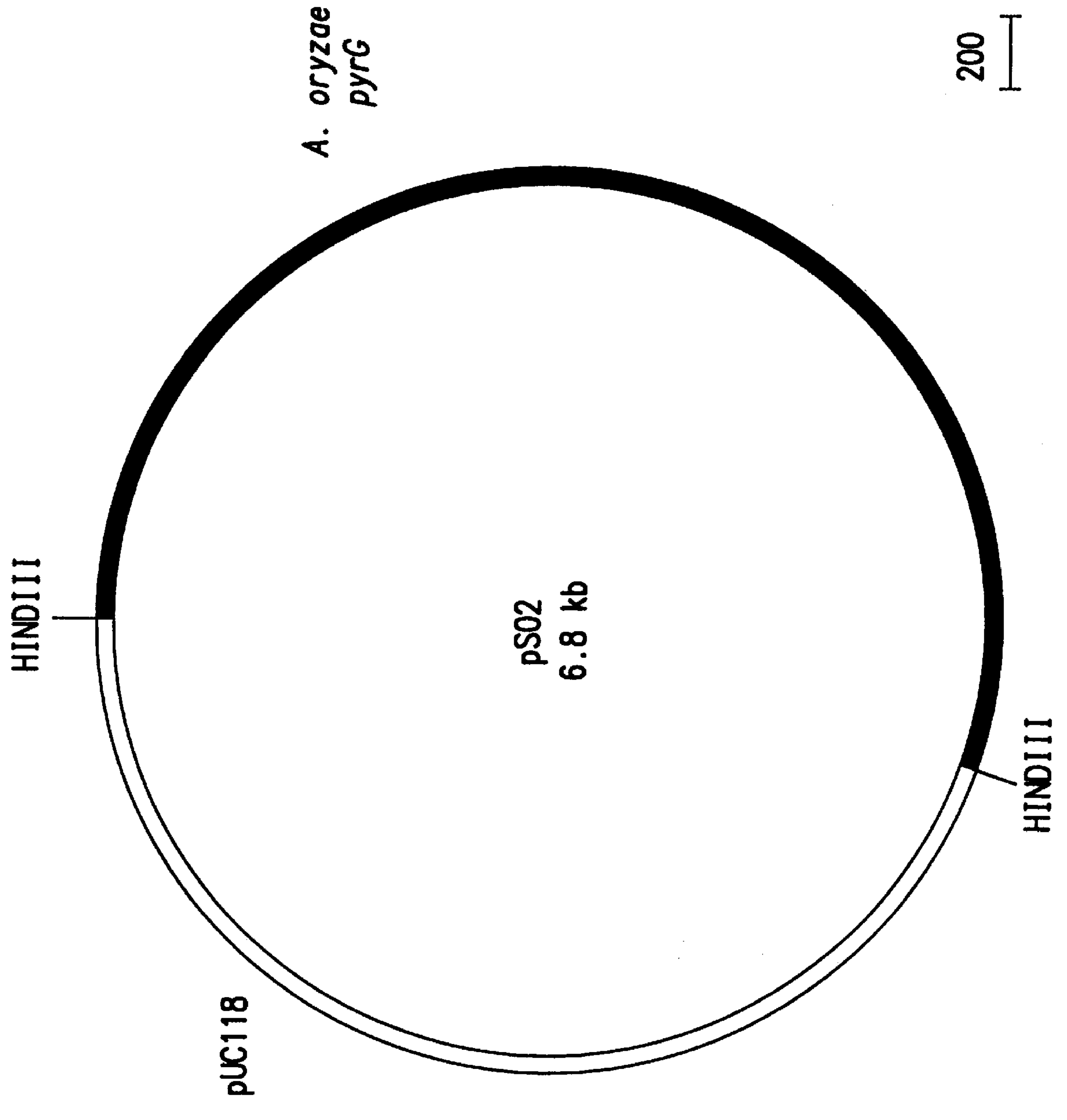
FIG. 5 shows a map of plasmid pSO2.

A 2102 bp BamHI/NruI genomic prepro-p45 protease fragment is inserted between a TAKA amylase promoter and amyloglucosidase (AMG) terminator. To accomplish this, the 5'-end of the gene is modified using PCR techniques to introduce a BamHI site directly upstream of the ATG initiation codon. At the 3'-end of the gene, the endogenous NruI site 44 bp downstream from the termination codon is used. The p45 expression plasmid is called pDM120 (FIG. 4). A pyrG- *A. oryzae* host strain is co-transformed with plasmids pDM120 and pSO2. Plasmid pSO2 contains the *A. oryzae pyrG* marker (see FIG. 5).

The transformation of *A. oryzae* is performed by the protoplast method (Christensen et al. Biotechnology 6:1419–1422 (1988), Yelton et al. Proceedings of the National Academy of Sciences (USA) 81:1470–1474 (1984) ). Typically, *A. oryzae* mycelia are grown in a rich nutrient broth. The mycelia are separated from the broth by a technique such as filtration, centrifugation, etc. The enzyme preparation Novozyme® (Novo Nordisk) is added to the mycelia in osmotically stabilizing buffer such as 1.2 M $MgSO_4$ buffered to pH=5.8 with sodium phosphate. The suspension is incubated for 60 minutes at 30° C. with agitation. The protoplasts are harvested and the protoplasts are resuspended in a osmotically stabilizing buffer containing calcium such as STC (1.2M sorbitol, 10 mM $CaCl_2$, 10 mM Tris-HCl pH=7.5). Transforming DNA is added to ca. 100 $\mu$l protoplast suspension and then 200 $\mu$l PEG solution (60% PEG 4000, 10 mM $CaCl_2$, 10 mM Tris-HCl, pH=7.5 is added and the mixture is incubated for 20 minutes at room temperature. An additional 1 ml polyethylene glycol solution is added and the solution is incubated again for 20 minutes at room temperature. The transformed protoplasts are diluted with 8 ml STC buffer and plated to selective plates. Acetamide (as sole nitrogen source for growth) plates can be used to select for transformants containing an exogenously supplied amds marker. Minimal plates can be used for transformants containing an exogenously supplied pyrG gene.

Transformants are grown in M400Da medium (maltodextrin, 50.0 g/L; $MgSO_4.7H_2O$, 2.0 g/L; $KH_2PO_4$, 2.0 g/L; citric acid, 4.0 g/L; yeast extract, 8.0 g/L; urea, 2.0 g/L; trace metals solution (as described earlier), 0.5 ml/L; pH=6.0 with 5N NaOH) at 25° C. and the broths analyzed for the production of p45 by SDS/PAGE. A major band migrating at ca. 45 kD is seen in at least one transformant, strain DLM7, and no p45 is seen in control cultures. The recombinant p45 produced in DLM7 is analyzed by protein sequence analysis and the N-terminal residues match-the mature N-terminus of p45 produced from *F. oxysporum*. Therefore, the p45 is processed correctly when made in *A. oryzae*.

Figure 6:
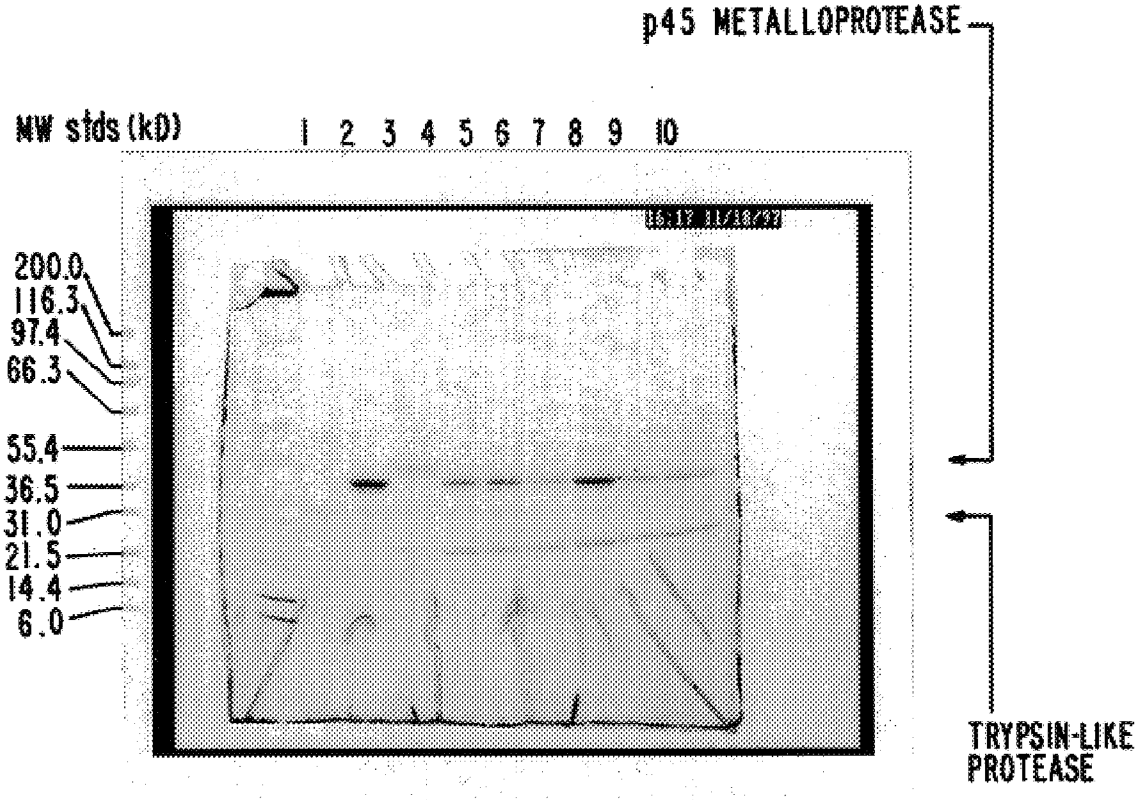
FIG. 6 shows SDS-PAGE analysis of *A. oxyzae* transformants containing both the pro *F. oxysporum* trypsin-like protease and the *F. oxysporum* p45 metalloprotease genes. The lanes contain supernatants from: lane 1, molecular weight markers; lane 2, control A. oryzae strain (untransformed); lane 3, A. oxyzae transformed with p45 only; lane 4, *A. oryzae* transformed with pSX183 trypsin-like protease only; lanes 5–10, *A. oryzae* strains transformed with both p45 and the pro *F. oxysporum* trypsin-like protease.

In order to make a host organism that expresses both the p45 and the trypsin-like protease, strain DLM7 is co-transformed with plasmids pSX233 containing the trypsin-like protease and pToC90 containing the *A. nidulans amdS* gene as a selectable marker. Plasmid pSX233 is a derivative of plasmid pSX183 in which the DNA linker at the beginning of the precursor trypsin-like protease gene has been changed from GGATCCTCGAATTCTCTTCA-GATCTCTTCACCATGG (SEQ ID NO:9) to GGATCCAC-CATGG (SEQ ID NO:10) using standard techniques of molecular biology. The underlined ATG indicates the position of the initiator methionine codon. Co-transformants are grown in FG4P medium and analyzed for *F. oxysporum* trypsin-like protease activity using the L-BAPNA assay. Six of the transformants made significantly more trypsin-like protease than a control strain that did not contain the p45. Supernatants from these transformant cultures (and controls) are analyzed by SDS/PAGE (FIG. 6). All transformants showed the production of both trypsin-like protease and p45 from the same host organisms. The results show that co-expression of the (precursor) trypsin-like protease and the *F. oxysporum* p45 in the same host cells (*A. oryzae*) results in significantly enhanced expression of active trypsin-like protease.

Example 4: Purification and Initial Characterization of a Neutral Metalloprotease (npI) from *Aspergillus oryzae*

Materials and Methods

Purification:

A 10 1 *A. oryzae* IFD 4177 fermentation is harvested. 9 1 of broth is obtained and filtered through a 0.1 μm hollow fibre (Amicon) and concentrated to 700 ml on a 3 kDa cut off spiral ultrafiltration cartridge (Amicon).

300 ml is diluted to 1000 ml (<1.5 mS, pH 7.1) and loaded onto a 150 ml (2.6 cm i.d.) Q-Sepharose column equilibrated in 0.1 M borate, 10 mM DMG, 2 mM $CaCl_2$, pH 6.2 at a flow rate on 5 ml/min. The column is washed with buffer and eluted with a 0->1M NaCl gradient in 1050 ml at 6 ml/min. 12 ml fractions are collected and assayed for metalloprotease activity for pro-trypsin-like *Fusarium oxysporum* protease disclosed, supra, activity. Metalloprotease containing fractions are pooled and concentrated on a YM3 membrane.

The pool is then diluted to 80 ml (<1.5 mS, pH 7.5), loaded onto a 20 ml MonoQ-column (1.6) cm i.d.) equilibrated in 20 mM Tris, 2 mM $CaCl_2$, pH 7.5 and eluted in a 0->0.5 M NaCl gradient in 300 ml at a flow rate on 6 ml/min). 4.5 ml fractions are collected and tested for metalloprotease activity. Fractions having activity are pooled and concentrated on Centriprep-10.

3 ml of MQ1 is subjected to gel filtration using a HiLoad Superdex 200 16/60 column equilibrated in 100 mM borate, 10 mM DMG, 2 mM $CaCl_2$, pH 6.2 at a flow rate of 1 ml/min. 1 ml fractions are collected. Fractions having metalloprotease activity are pooled.

A further purification step is established by doing pilot runs on either phenyl-superose 5/5 (flow rate 0.5ml/min, 1.7->OM $(NH_4)_2S0_4$ gradient in 60 min in 25 mM Tris pH 7, 1 ml fractions collected) or bacitracin coupled to CH Sepharose 4B (15 ml column 1.6 cm i.d., flow rate: 2 ml/min, 0->100% B in 80 min (A: 25 mM acetate, pH 5, B: 0.1M Tris, 1M NaCl, 25% isopropanol, pH 7.5), 3 mL fractions collected). 2 ml of S2 is desalted on PD-10 for each run (eluted in 3.5 ml of the respective buffers), 3 is is loaded. Fractions having metalloprotease activity are pooled. A larger amount is purified using the bacitracin-column; 3 ml S12+3 ml S13+1 ml S2 is desalted on PD-10 into 25 mM acetate, pH 5 and 10 ml is loaded on the column. Fractions having metalloprotease activity are pooled and concentrated on Centricon-10 and Microcon-10).

Coupling of Bacitracin:

Coupling of bacitracin to activated CH Sepharose 4B (Pharmacia) is performed according to manufacturer's descriptions. 6.6 g CH Sepharose (swell in 1 mM HCl and washed in coupling buffer) is used and coupled with 0.25 g (18250 units) of bacitracin (Sigma) in 0.1M $NaHCO_3$, 0.5M NaCl, pH 8 for 2 hours at room temperature. Excess active groups are blocked with 0.1 M Tris, pH 8 followed by washing with 0.1M acetate, 0.5M NaCl, pH 4.

Enzyme Assay:

The activity of npI is measured as released trypsin activity from pro-trypsin-like *Fusarium oxysporum* protease disclosed, supra (~25 μg/ml) after a 30 min pre-incubation at 25° C. in 0.1M Tris, 2 mM $CaCl_2$, pH 7.5. The tryptic activity is measured in microtiter plates: 100 μl of substrate (Stock: 87 mg/ml L-BAPNA (Sigma) in DMSO, diluted 50 fold in buffer) and the absorption at 405 nm is measured using Thermomax microplate reader from Molecular Devices.

SDS-PAGE and Electroblotting onto PVDF:

SDS-PAGE (10–27%, Novex) are run according to the manufacturer's instructions (125 V, 2 hours); samples to be run is preincubated with PMSF (0.2%) before adding sample buffer. Electroblotting onto pro-blot membranes (Applied biosystems) is performed in 3 mM $Na_2CO_3$, 10 mM $NaHCO_3$, 20% MeOH, pH 9.9 at 25V for 2.5 hours using the blotting module from Novex. The pro-blot is stained as described by Applied Biosystems.

IEF-Overlay:

IEF (Ampholine PAG-plate: pH 3.5–9.5, Pharmacia) is run (1500V, 50 mA, 1.25 hour) and stained according to the manufacturer's instructions. The gel to be overlaid is first equilibrated for 15 min in 0.1M Tris, 2 mM $CaCl_2$, pH 7 and then overlaid with 1% agarose, 0.1 M Tris, 2 mM $CaCl_2$, pH 7 added L-BAPNA stock (50-fold diluted) and pro-trypsin-like *Fusarium oxysporum* protease disclosed, supra (crude concentrated broth 1 mg/ml, 50 fold diluted). Casein overlay is performed by having 1% skimmed milk in the overlay buffer.

Amino Acid Sequencing:

Amino acid sequencing is done using the 476A Protein Sequencer from Applied Biosystems according to manufacturer's instructions; premixed buffers are used for the online-HPLC.

Results

Figure 7:
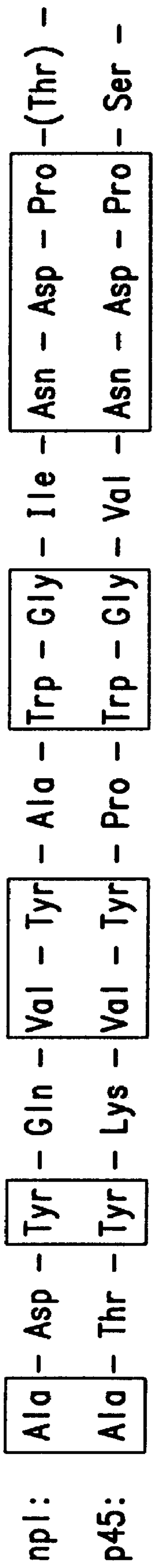
FIG. 7 shows a comparison of the N-terminal amino acid sequence of purified npI with p45.

The purification procedure described supra results in a more than 3300 fold purification (purity >95% (SDS- PAGE). The purified npI has a molecular weight around 46 kDa from SDS-PAGE and a pI around 4.5 from IEF. An overlaid IEF-gel (overlaid with pro-trypsin-like *Fusarium oxysporum* protease disclosed, supra and L-BAPNA) shows that the proteolytic or metalloprotease activity occurs around pI 4.5, where casein clearing is also seen. When the purified npI is subjected to N-terminal amino acid sequencing, one sequence is obtained (the first few cycles contained some background). This amino acid sequence corresponds to the N-terminal amino acid sequence obtained from the 46 kDa band blotted from an SDS-gel on a PVDF-membrane; giving the amino acid sequence reported in FIG. 7. The N-terminal amino acid sequence is 64% homologous to the N-terminal sequence for p45 from *F. oxysporum* (FIG. 7). The protease pH-optimum is found to be around 5.5–6.0. Incubations with pro-trypsin-like *Fusarium oxysporum* protease disclosed, supra are performed in dilute buffers at various pHs.

Example 5: Comparison of Ability of p45 Metalloprotease with Other Neutral Metalloproteases in Hydrolyzing Casein 400 ul of casein solution (Pierce) is added to small test tubes along with 100 ul of protease. The tubes are vortexed and incubated at room temperature for 40 minutes. The incubation (and assay) buffer is 0.1 M borate, 2 mM $CaCl_2$, and 10 mM dimethylglutarate, pH 6.5. At the end of the incubation, 60 microliters of trichloroacetic acid (100% w/v) is added, and the tubes are vortexed and centrifuged for 1 minute at 5000×g. 20 microliters of the resulting supernatant is placed into a microtiter plate well with 200 microliters of the BCA working reagent (Pierce). The plates are then vortexed and incubated another 30 minutes, then read at 600 nm using a Biomek 1000 microtiter plate reader.

Figure 8:
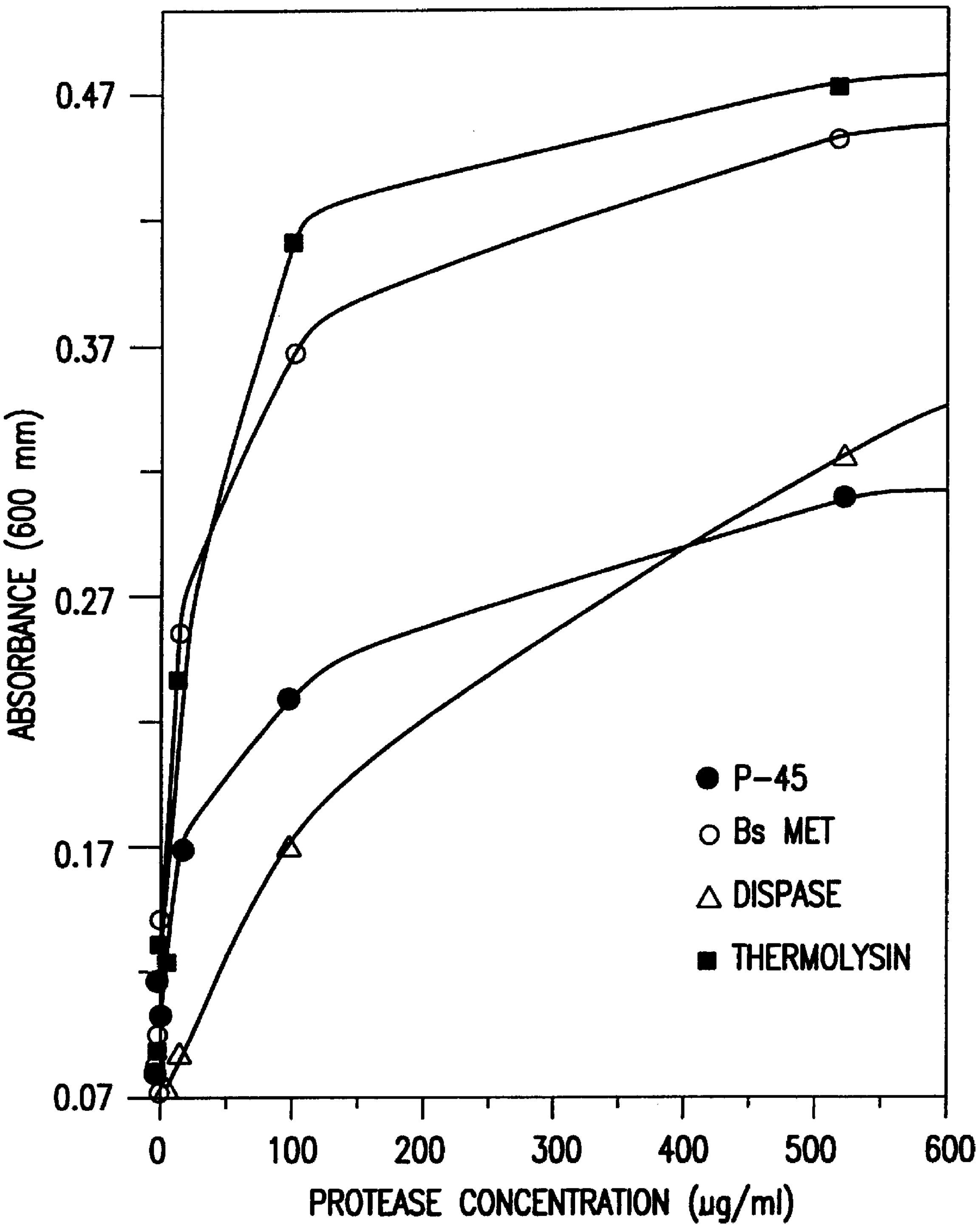
FIG. 8 shows a comparison of neutral protease activities using the succinylated casein assay.

The data shown in FIG. 8 demonstrates that p45 has the lowest proteolytic activity when compared to thermolysin, dispase and the neutral metalloprotease from *Bacillus stearothermophilus* (Bs mat) all appear to hydrolyze casein to a greater extent than the p45, i.e. all three have a maximum absorbance near or above 0.47. However, the maximum absorbance when using p45 appears to be around 0.3 O.D. units (about 60% that of the other three proteases).

Example 6: Characterization of Recombinant p45

Materials and Methods

Reagents:

Thermolysin from *Bacillus thermoproteolyticus* (B.t.) is purchased from Boehringer Mannheim. FAGLA; N-(3-[2-Furyl]Acryloyl)-Gly-Leu is purchased from Sigma. Ac-Pro-Leu-Gly[2-mercapto-4-methyl-pentanoyl]-Leu-Gly-OEt is purchased from Bachem. Ellman's reagent (5,5'-dithiobis(2-nitrobenzoic acid); DTNB) and p-nitroaniline are purchased from Sigma.

100 mg of pentapeptide (pyroGlu-Glu-Ile-Pro-Asn-COOH; 87% pure as judged by HPLC) is purchased from Chiron Mimotopes Peptide Systems (3550 General Atomics Court, San Diego, Calif. 92121-1122). The pentapeptide is further purified (HPLC, 0–60% Acetonitrile gradient in 0.1% TFA) before biochemical analysis.

Universal buffer (0.1M borate, 0.1M acetic acid, and 0.1M phosphoric acid) is the "modified" buffer of Britton & Robinson (Quelle: Biochemisches Taschenbuch, H. M. Rauen, II. Teil, s.93 u. 102, 1964). Trypsin-like *F. oxysporum* protease sample buffer consists of 0.1M borate, 2 mM $CaCl_2$, and 10 mM dimethyl glutarate, pH 6.5.

SDS-PAGE Analysis:

For SDS-PAGE analysis, 30 microliters of sample are added to 10 microliters of SDS-PAGE sample buffer, 2 microliters of PMSF (2% in isopropanol), and 2 microliters of glycerol. The samples are placed in boiling water for 4 minutes and 40 microliters are loaded into each well of the gel (Novex, 10–27% gradient gel). Gels are run for approximately 2-hours at 125 V and then processed using standard protocols.

Isoelectric Focusing Analysis:

p45 metalloprotease is loaded onto a normal IEF gel (Novex; pH 3–10) and the standard Novex IEF protocol is performed (1-hour @ 100V, 1-hour g 200V, and 0.5-hour @ 500V). The gel is fixed and stained (Coomassie) according to standard Novex protocols.

p45 Metalloprotease Purification:

2300 ml of broth (pH=6) containing recombinant p45 metalloprotease in Aspergillus oryzae is concentrated to approximately 300 ml using a S1Y-3 spiral membrane cartridge (3 kDa MW cutoff; Amicon). The solution is concentrated further to 175-ml using a PM-10 membrane (Amicon), a membrane with a known molecular weight cutoff of 10 kDa. Following concentration, the solution is adjusted to pH 5 with glacial acetic acid and diluted to 950 ml with water to a final conductivity of 1.6 mS.

The solution is loaded onto an SP-Sepharose (cation-exchange) column (1.6×29 cm) pre-equilibrated in buffer containing 0.1M borate, 2 mM $CaCl_2$, 10 mM dimethyl glutarate, pH 5.2, and subsequently washed with 70 ml of the same buffer. A 0–0.5 M NaCl gradient is used to elute the recombinant p45 metalloprotease which bound to the column. The flow rate is 4 ml/min. and 10 ml fractions are collected. The metalloprotease eluted as a single peak at approximately 0.17M NaCl.

Fractions containing the partially-purified p45 metalloprotease are pooled and immediately adjusted to pH 7.2 with NaOH, then stored at −20° C. SDS-PAGE analysis of the purified preparation reveals quite pure protein (>95%). Three to four major bands are observed (with approximate molecular weights of 9, 11.5, 26, and 44 kDa) are sequenced and shown to be p45 metalloprotease.

The solution is further concentrated to 1.75 ml using a PM-10 membrane; a membrane with a known molecular weight cutoff of 10 kDa. The final concentration of the recombinant p45 metalloprotease from this preparation is 13.35 mg/ml.

Pro-Trypsin-Like *F. oxysporum* Protease Purification:

3000 ml of fermentation broth from *Fusarium oxysporum* is concentrated to approximately 250 ml using a S1Y-3 spiral membrane cartridge (Amicon). Following concentration, the solution is adjusted to pH 5 with glacial acetic acid and diluted to 2000 ml with water to a final conductivity of 1.0 mS.

A portion of the solution containing the recombinant pro-trypsin-like *F. oxysporum* protease (85 ml) is loaded onto a SP-sepharose (cation-exchange) column (1.6×29 cm) pre-equilibrated in buffer containing 0.1M borate, 2 mM $CaCl_2$, and 10 mM dimethyl glutarate, pH 5.2, and washed with 70 ml of the same buffer. A 0–0.5M NaCl gradient is used to elute pro-trypsin-like *F. oxysporum* protease bound to the column. The flow rate is 4 ml/min. and 10 ml fractions are collected. Pro-trypsin-like *F. oxysporum* protease eluted as a single peak which is followed by one other peak which contained tryptic activity. This procedure is performed two more times so as to purify the remaining pro-trypsin-like *F. oxysporum* protease.

Fractions from the three cation-exchange purification steps (containing the partially-purified pro-trypsin-like *F. oxysporum* protease) are pooled and adjusted to pH 7.2 with NaOH and stored at −20° C. As with the p45 metalloprotease, SDS-PAGE analysis of the purified preparation revealed quite pure protein (>95%). The solution is further concentrated to 8-ml using a PM-10 membrane; a membrane with a known molecular weight cutoff of 10 kDa. The final concentration of the recombinant p45 metalloprotease from this preparation is 25.45 mg/ml.

Trypsin-Like *F. oxysporum* Protease Standard:

Recombinant trypsin-like *F. oxysporum* protease standard is purified from fermentation broths of either *Aspergillus oryzae* or *Fusarium graminearum* using Q-Sepharose (anion-exchange) and SP-Sepharose (cation-exchange) chromatography. Fermentation broth (950 ml; approximately 3 grams of trypsin-like *F. oxysporum* protease) is filtered (0.22 micron membrane; Corning disposable sterile bottle top filter), and loaded onto a Q-Sepharose (anion-exchange) column (2.6×24 cm; 127 ml) pre-equilibrated in sample buffer. The eluate (1 L) is collected, concentrated to 200 ml on an S1Y3 spiral cartridge (3K MW cutoff; Amicon), and subsequently diluted to 1 L with water (conductivity =2 mS).

200 ml of diluted eluate (600 mg of trypsin-like *F. oxysporum* protease) is loaded onto an SP-Sepharose column (1.6×26 cm; 53 ml) pre-equilibrated in sample buffer. The column is washed with 2 column volumes of sample buffer and a 0–1M NaCl gradient elution is performed. Purified trypsin-like *F. oxysporum* protease eluted as a single band with approximately 100 mM NaCl. The sample is concentrated (Centriprep 10, Amicon), glycerol is added to a final concentration of 50%, and the sample (50 ml; 9 mg/ml trypsin-like *F. oxysporum* protease) is stored at −20° C.

Trypsin-Like *F. oxysporum* Protease Assay:

Trypsin-like *F. oxysporum* protease activity is measured in microtiter wells which included trypsin-like *F. oxysporum* protease in sample buffer (i.e. 0.1M borate, 2 mM $CaCl_2$, 10 mM DMG, pH 6.5; total volume =100 microliters), and 100 microliters of substrate (87 mg/ml L-BAPNA stock in DMSO diluted 50-fold in sample buffer). Trypsin-like *F. oxysporum* protease activity is determined as an increase in absorbance at 405 nm (via a Thermomax microtiter plate reader, Molecular Devices Inc.) immediately after L-BAPNA addition.

Pro-Trypsin-Like *F. oxysporum* Protease Assay:

Activatable pro-trypsin-like *F. oxysporum* protease is determined in microtiter wells as released trypsin-like *F. oxysporum* protease (tryptic) activity from pro-trypsin-like *F. oxysporum* protease after a 40 minute pre-incubation at room temperature with purified *Fusarium oxysporum* metalloprotease (approximately 6 ug).

Processed pro-trypsin-like *F. oxysporum* protease(i.e. mature trypsin-like *F. oxysporum* protease) activity is determined directly from microtiter plates containing the pre-incubated metalloprotease/pro-trypsin-like *F. oxysporum* protease cocktail (total volume=100 microliters), and 100 microliters of substrate (87 mg/ml.L-BAPNA stock in DMSO diluted 50-fold in sample buffer). Again, active trypsin-like *F. oxysporum* protease is determined as an increase in absorbance at 405 nm immediately after L-BAPNA addition.

Protease Analysis Using FTC-labeled Casein:

FTC-labeled casein is prepared according to the method of Twinning, 1984, Anal. Biochem. 143:30. FTC-casein (20 microliters, 0.5% w/w in 50 mM Tris-Cl, pH 7.2), and protease (10 microliters in sample buffer, approximately 0.9 ug) are added to sample buffer (10 microliters, 50 mM sodium borate, pH 9). Samples are incubated at room temperature for 30 minutes. At the end of the incubation, 150 microliters of 5% (w/v) trichloroacetic acid is added and the samples are allowed to precipitate for 60 minutes at 4° C. Samples are subsequently centrifuged (14,000 rpm, 5 minutes) and 30 microliters of supernatant are added to 3 ml of 0.5M sodium borate, pH 9.

The fluorescence of the samples is measured (Perkin-Elmer fluorimeter) using a 2.5 nm slit width, excitation at 490 nm and emission detected at 525 nm.

Casein Hydrolysis by Recombinant p45 Metalloprotease and Other Metalloproteases Using the QuantiCleave Method 400 microliters of casein solution (Pierce) are added to small test tubes along with 100 microliters of protease in buffer "A" (0.1M borate, 2 mM $CaCl_2$ and 10 mM dimethylglutaric acid). At the end of the incubation, 60 microliters of trichloroacetic acid (100% w/v) is added, and the tubes are vortexed and centrifuged for 1 minute at 5000×g. 20 microliters of the resulting supernatant is placed into a microtiter plate well with 200 microliters of the BCA working reagent (Pierce). The plates are then vortexed and incubated another 30 minutes, then read at 600 nm using a Biomek 1000 microtiter plate reader.

Hydrolysis of the Thermolytic Substrate: AC-Pro-Leu-Gly[2-mercapto-4-methyl-pentanoyl]-Leu-Gly-OEt The thermolytic substrate Ac-Pro-Leu-Gly[2-mercapto-4-methyl-pentanoyl]-Leu-Gly-OEt (i.e. the merc-peptide) is also used to further characterize the p45 metalloprotease and B.t. thermolysin.

Reaction mixtures contain 100 microliters of Ac-Pro-Leu-Gly[2-mercapto-4-methyl-pentanoyl]-Leu-Gly-OEt (1 mM, and 1 mM Ellman's reagent) and 100 microliters of either B.t. thermolysin or purified p45 metalloprotease (0–3 ug/ml) in sample buffer. Thermolytic activity is determined as an increase in absorbance at 405 nm over 2 minutes on a microtiter plate reader (Molecular Devices).

FAGLA Hydrolysis by p45 Metalloprotease and Thermolysin:

The thermolytic substrate FAGLA: N-(3-[2-Furyl] Acryloyl)-Gly-Leu amide is used to further characterize the p45 metalloprotease and B.t. thermolysin. Reaction mixtures contain 100 microliters of N-(3-[2-Furyl]Acryloyl)-Gly-Leu amide (FAGLA) (2 mM) and 100 microliters of various concentrations of either thermolysin (Boehringer Mannheim) or purified p45 metalloprotease. Thermolytic activity is determined as a decrease in absorbance at 345 nm on the recording spectrometer for one minute(Shimadzu, UV160U). The linear range of the assay for thermolysin is 10–500 ug/ml thermolysin in the assay mix.

p45 Metalloprotease Thermal Stability:

Purified p45 metalloprotease or B.t. thermolysin (Boehringer Mannheim) (50 microliters, 0.1 mg/ml) are incubated at various temperatures for 15-minutes in Universal buffer, pH 7. Ten microliters of sample are then added to 30 microliters of Universal pH buffer (pH 7) and 20 microliters of FTC-labeled casein and are incubated at 37° C. for 1 hour. 150 microliters of 5% TCA is added to acidify and precipitate casein (1 hour at room temperature). Samples are then centrifuged (5 minutes, 14K rpm) and 30 microliters of supernatant are added to 3 ml buffer (0.5M borate, pH 9). Samples are then analyzed on the fluorimeter (slit width=2.5 nm; excitation freq.=490 nm; emission freq.=525 nm; integration time=2 sec).

p45 Metalloprotease pH Profile:

Purified p45 metalloprotease (10 microliters, 0.005 mg/ml) is added to 30 microliters of Universal pH buffer (pH 5–11.5), and 20 microliters of FTC-labeled casein are incubated at 37° C. for 1-hour. 150 microliters of 5% TCA is added to acidify and precipitate casein (1-hour at room temperature). Samples are then centrifuged (5 minutes, 14K rpm)and 30 microliters of supernatant are added to 3-ml buffer (0.5M borate, pH 9). Samples are then analyzed on the fluorimeter (slit width=2.5 nm; excitation freq.=490 nm; emission freq.=525 nm; integration time=2 sec).

A second pH profile is determined utilizing the pro-trypsin-like *F. oxysporum* protease assay whereby p45 metalloprotease activity is determined based on the processing of pro-trypsin-like *F. oxysporum* protease to active trypsin-like *F. oxysporum* protease Reaction mixtures contain 125 ug of purified pro-trypsin-like *F. oxysporum* protease and 0.13 ug of purified p45 metalloprotease (i.e. a molar ratio of pro-trypsin-like *F. oxysporum* protease/ p45=1750:1) are added to "universal-buffer" solutions prepared at different pH's (i.e. pH values of 2.72, 4.11, 5.2, 6.05, 6.46, 6.98, 8.18, 9.02, 10.03, and 11.01) and the reaction mixtures are incubated for 15 minutes at room temperature. After incubation, 5 microliters are taken from each sample and added to microtiter wells containing 90 microliters of sample buffer (i.e. 0.1M borate, 2 mM $CaCl_2$, and 10 mM DMG, pH 6.5), and 10 microliters of phosphoramidon (20 ug). Trypsin-like *F. oxysporum* protease activity is determined from each sample immediately after the addition of 100 microliters of L-BAPNA (1.74 mg/ml) to each well. Phosphoramidon is added to inhibit p45 activity and stop any further maturation of pro-trypsin-like *F. oxysporum* protease.

p45 Metalloprotease pH Stability

To determine the pH stability of the recombinant p45 metalloprotease, the partially-purified p45 metalloprotease is diluted 10-fold into universal buffers at pH's of 3.5,4,4.5, 5.2, 5.64, 6, 7, 8, 9, and 10 and pre-incubated at room temperature for 20 minutes. The pre-incubated samples (10 microliters) are added to 40 microliters of buffer containing 0.1M borate, 2 mM $CaCl_2$, and 10 mM dimethylglutarate, pH 6.5 and 50 microliters of crude A. oryzae broth containing pro-trypsin-like *F. oxysporum* protease and subsequently incubated another 30 minutes. After 30 minutes, 100 microliters of BAPNA (approx. 2 mg/ml) in sample buffer is added and the increase in absorbance at 405 nm over a 5 minute time course is determined to assay for trypsin-like *F. oxysporum* protease activity.

NaCl Inhibition of p45 Metalloprotease Activity:

FTC-labeled casein is prepared according to the method of Twinning (1984). FTC-casein (20 microliters, 0.5% w/w in 50 mM Tris-Cl, pH 7.2), NaCl (0–2M) in trypsin-like *F. oxysporum* protease sample buffer, and either trypsin-like *F. oxysporum* protease (10 microliters, 1.8 ug) or p45 metalloprotease (10 microliters, 0.33 ug) are added to trypsin-like *F. oxysporum* protease sample buffer to a total volume of 50 microliters. Samples are incubated at room temperature for 30 minutes. At the end of the incubation, 150 microliters of 5% (w/v) trichloroacetic acid is added and the samples are allowed to precipitate for 60 minutes at 4° C. Samples are subsequently centrifuged (14,000 rpm, 5 minutes) and 30 microliters of supernatant are added to 3 ml of 0.5M sodium borate, pH 9.

The fluorescence of the samples is measured (Perkin-Elmer fluorimeter) using a 2.5 nm slit width, excitation at 490 nm and emission detected at 525 nm.

Figure 9:
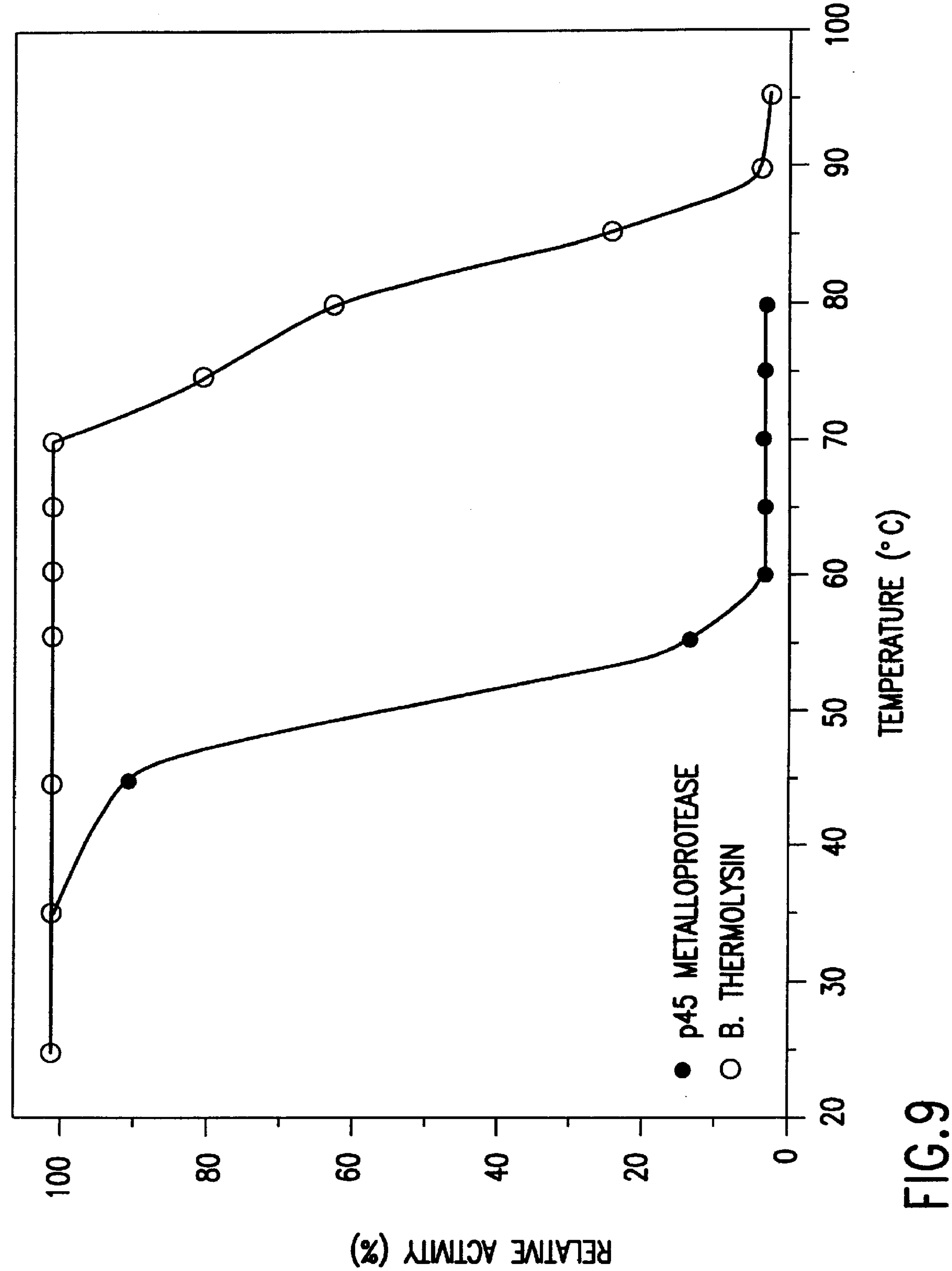
FIG. 9 shows thermal stability profiles of the p45 metalloprotease and the *Bacillus thermolysin.*
Figure 10:
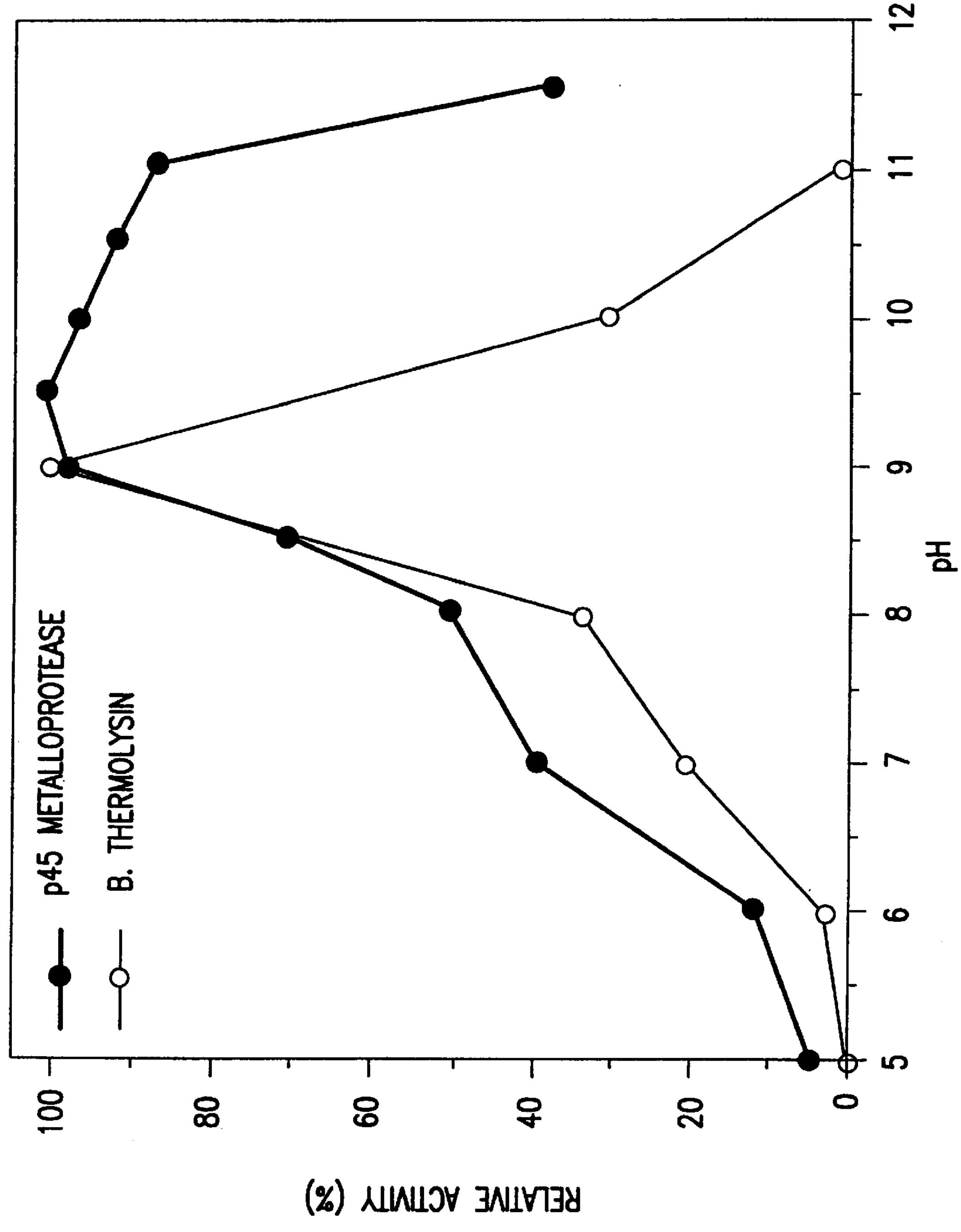
FIG. 10 shows pH profiles of p45 metalloprotease and the *Bacillus thermolysin.*

Results and Discussion:

p45 Metalloprotease Thermal Stability:

The optimum temperature at which the p45 metalloprotease will hydrolyze the substrate FTC-casein is 50° C. This result is significantly lower than that of thermolysin from *Bacillus thermoproteolyticus* (80° C.) (FIG. 9).

p45 Metalloprotease pH Profile:

Hydrolysis of FTC-casein by the p45 metalloprotease is determined in universal pH buffers (pH 5–11.5). The optimum pH for p45 metalloprotease hydrolysis of FTC-casein is pH 9.5 (FIG. 10). Note that the profile is somewhat broad (>50% maximum activity occurs between pH 8 and 11.5), much broader than that of thermolysin from *Bacillus thermoproteolyticus.*

A second pH profile is determined utilizing the pro-trypsin-like *F. oxysporum* protease assay whereby p45 metalloprotease activity is determined based on the processing of pro-trypsin-like *F. oxysporum* protease to active trypsin-like *F. oxysporum* protease. Maximum levels of processed pro-trypsin-like *F. oxysporum* protease occur at a pH of 9.5. It is important to note that the time course of this experiment never allows the p45 metalloprotease to fully process all of the available pro-trypsin-like *F. oxysporum* protease-it takes at least 25 minutes to fully process the available pro-trypsin-like *F. oxysporum* protease under these conditions. In addition, under these conditions, the level of processed pro-trypsin-like *F. oxysporum* protease at pH 6.5 is approximately 24% the level of processed pro-trypsin-like *F. oxysporum* protease at pH 9.

p45 Metalloprotease pH Stability:

The p45 metalloprotease appears to be most stable at pH 8. However, the peak is somewhat broad with an acceptable pH range of pH 6.5–9.

TABLE 2

Substrate Specificity Analysis of the p45 Metalloprotease and Thermolysin from *Bacillus stearothermophilus* (*B.s.*).

| | Specific Activity | |
|---|---|---|
| Substrate | p45 Metalloprotease | B.s. Thermolysin |
| pro-trypsin | 1.2 g trypsin/min*mg | .018 g trypsin/min*mg |
| merc-peptide | 57 AU/min*mg | 2.9 AU/min*mg |
| FAGLA | 0.76 -AU/sec*mg | 227 -AU/sec*mg |
| Succinylated Casein** | 0.30 O.D | 0.47 O.D. |
| FTC-Labelled Casein | 170 FU/min*mg | 220 FU/min*mg |
| Ala—Ala—Ala-pNA | <2 pmol pNA/min*mg | <2 pmol pNA/min*mg |

*NOTE:
AU, FU, FTC-, and pNA are designated as absorbance units, fluoresence units, fluorescein-, and para-nitroanilide respectively. The merc-peptide and FAGLA are the thermolytic substrates Ac—Pro—Leu—Gly-[2-mercapto-4-methyl-pentanoyl-Leu—Gly-—Et and N-(3-[2-Furyl]Acryloyl)-Gly—Leu amide, respectively.
**Although the initial rates of hydrolysis were similar, maximal levels of hydrolyzed casein by p45 metalloprotease did not exceed 60% that of the maximum observed using the B.s. thermolysin.

Recombinant p45 Metalloprotease Levels in Culture Broth Can Process at Least 10 g/L pro-Trypsin-Like *F. oxysporum* Protease.

Purified pro-trypsin-like *F. oxysporum* protease is added to fresh *A. oryzae* fermentation broths containing the recombinant p45 metalloprotease (approximately 90 mg/L) and incubated for either 1, 2, or 3 hours at room temperature. Levels of pro-trypsin-like *F. oxysporum* protease in the incubation mixtures range from 100 ug/ml to 13 mg/ml.

Therefore, under these conditions, the recombinant p45 metalloprotease can easily process 80–100% of the activatable pro-trypsin-like *F. oxysporum* protease within a 1 hour time period.

Purified pro-trypsin-like *F. oxysporum* protease (100 ug/ml) is added to various amounts of either purified recombinant p45 metalloprotease or purified B.s. metalloprotease. It appears that one mole of the B.s. metalloprotease is required to process one mole of pro-trypsin-like *F. oxysporum* protease. However, under similar conditions, one mole of the p45 metalloprotease can process about 50 moles of pro-trypsin-like *F. oxysporum* protease within 1 hr. (see also Table 2).

The p45 metalloprotease becomes more efficient at processing pro-trypsin-like *F. oxysporum* protease as the concentration of pro-trypsin-like *F. oxysporum* protease increases since high pro-trypsin-like *F. oxysporum* protease levels (1–15 g/L) require less p45 metalloprotease (<100 mg/L) for processing.

Casein Hydrolysis by Recombinant p45 Metalloprotease and Other Metalloproteases.

Although the p45 metalloprotease is the best (processing) enzyme for maturation of pro-trypsin-like *F. oxysporum* protease to active trypsin-like *F. oxysporum* protease, it has the lowest proteolytic activity (when compared to other neutral metalloproteases) when hydrolyzing succinylated casein (Table 2). It is interesting to note that the 3 other neutral metalloproteases (i.e. thermolysin, Dispase, and the neutral metalloprotease from *Bacillus stearothermophilus*) all appear to hydrolyze casein to a greater extent than the p45 metalloprotease (i.e. all three have a maximum absorbance near 0.47). However, the maximum absorbance when using p45 metalloprotease appears to be around 0.3 O.D. units (about 60% that of the other three proteases). This data may indicate that the p45 metalloprotease may be a more specific protease than the other three neutral metalloproteases and thus hydrolyzes less casein.

Hydrolysis of the Thermolytic Substrate: Ac-Pro-Leu-Gly [2-mercapto-4-methyl-pentanoyl]-Leu-Gly-OEt The thermolytic substrate Ac-Pro-Leu-Gly[2-mercapto-4-methyl-pentanoyl]-Leu-Gly-OEt (i.e. the merc-peptide) is also used to further characterize the p45 metalloprotease and B.t. thermolysin. The p45 metalloprotease is about 25-fold more effective at hydrolyzing this thermolytic mercapto-peptide than B.s. thermolysin (Table 2).

FAGLA Hydrolysis by p45 Metalloprotease and Thermolysin:

The thermolytic substrate FAGLA: N-(3-[2-Furyl] Acryloyl)-Gly-Leu amide is used to further characterize the p45 metalloprotease and B.t. thermolysin. The linear range of the assay for thermolysin is determined to be 10–500 ug/ml thermolysin in the assay mix. The specific activity of the p45 metalloprotease for FAGLA is approximately 250 times lower than that of thermolysin.

p45 metalloprotease or B.s. Thermolysin do not Hydrolyze the Substrate Succ-Ala-Ala-Ala-pNA Both p45 metalloprotease and a neutral zinc endopeptidase secreted by Flavobacterium meningosepticum poorly hydrolyze the substrate N-[3-(2--furyl)acryloyl]-Leu-Gly-$NH_2$. However, the neutral zinc endopeptidase secreted by *Flavobacterium meningosepticum* will hydrolyze the vertebrate elastase substrate succinyl-Ala-Ala-Ala-p-nitroanilide, a substrate that thermolysin cannot hydrolyze (Table 2). Therefore, succinyl-Ala-Ala-Ala-p-nitroanilide hydrolysis by the p45 metalloprotease is investigated. However, neither, the p45 metalloprotease nor the B.s. thermolysin would hydrolyze succinyl-Ala-Ala-Ala-p-nitroanilide (4.4 mM) in 0.1M Tris, pH 8. This effect further differentiates the p45 metalloprotease from other existing metalloproteases.

The Pentapeptide does not Inhibit p45 Metalloprotease Activity:

The synthetic pentapeptide, <Glu-Glu-Ile-Pro-Asn (the peptide representing the pro-sequence of pro-trypsin-like *F. oxysporum* protease) is added to mixtures containing purified p45 metalloprotease and pro-trypsin-like *F. oxysporum* protease. After a 45-minute pre-incubation at room temperature with gentle shaking, the mixtures are diluted 500-fold and assayed for trypsin-like *F. oxysporum* protease activity. Note that after a 500-fold dilution, any pentapeptide present will not significantly inhibit trypsin-like *F. oxysporum* protease activity in the assay. Results demonstrate that the level of pentapeptide does not alter the normal processing of pro-trypsin-like *F. oxysporum* protease by the p45 metalloprotease and indicates that the peptide is not an inhibitor of p45 metalloprotease activity.

In addition, since the pentapeptide contains all residues on the amino-terminal of the p45 metalloprotease cleavage site, significant binding (and perhaps inhibition) of the p45 metalloprotease must occur at residues on the carboxy-terminal (P1'-P?') of the cleavage site.

Figure 11:
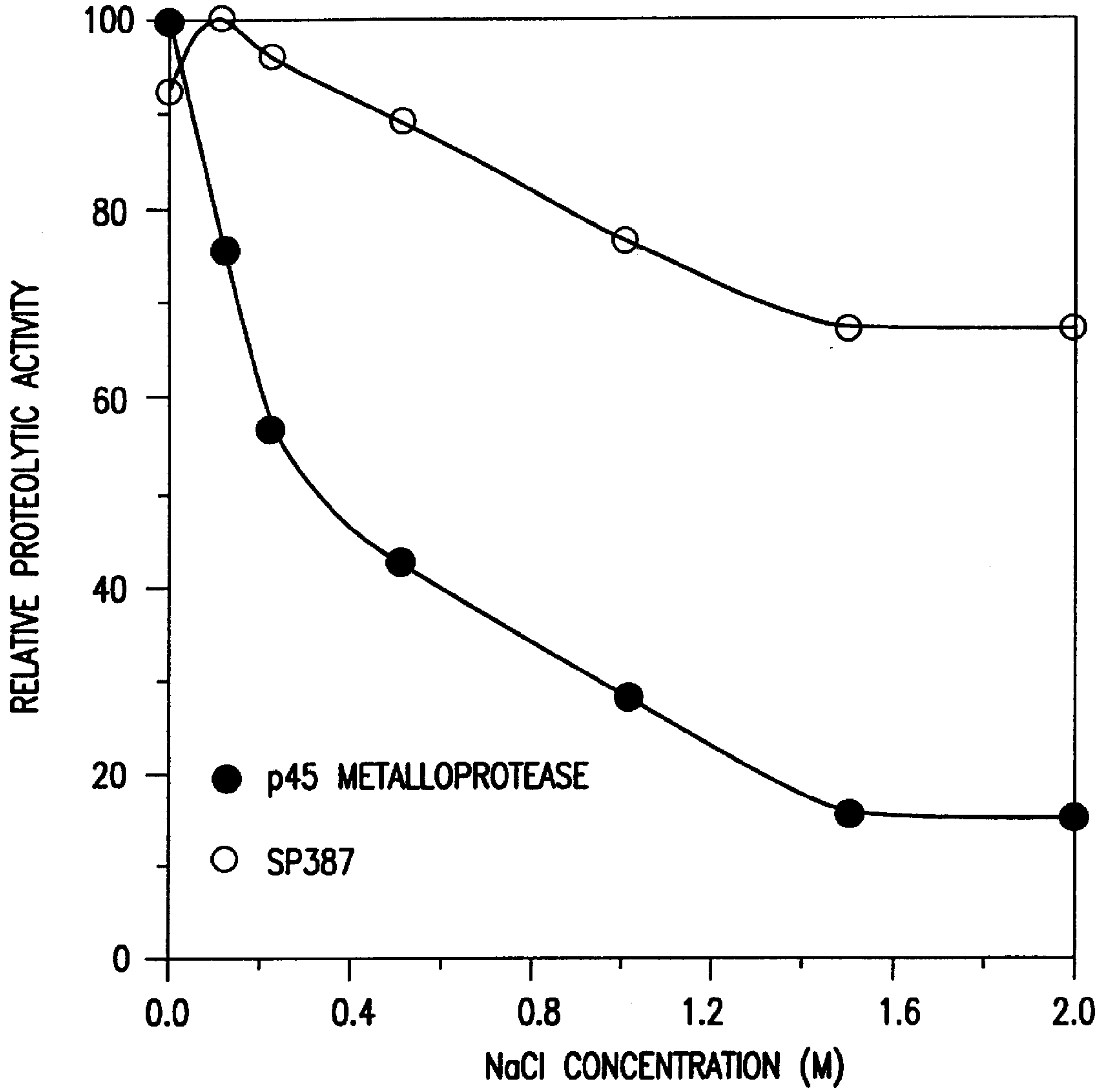
FIG. 11 shows salt tolerance of proteases.

NaCl Inhibition of p45 Metalloprotease Activity:

The p45 metalloprotease appears to be somewhat salt sensitive. 1M NaCl inhibits p45 metalloprotease activity by 85%, while trypsin-like *F. oxysporum* protease activity is only inhibited 25% using 2M NaCl (FIG. 11). The bacterial thermolysins are only inhibited 38% with 1M NaCl.

FTC-Casein Hydrolysis by p45 Metalloprotease vs Trypsin-Like *F. oxysporum* Protease:

Trypsin-like *F. oxysporum* protease and the p45 metalloprotease are both alkaline proteases (pI's>8) which function optimally at a pH near 9.5. However, the p45 metalloprotease will hydrolyze FTC-casein approximately 16-fold higher than trypsin-like *F. oxysporum* protease on a molar basis at pH 9. Therefore, the p45 metalloprotease may find utility in applications requiring an alkaline protease. It is interesting that fermentation of recombinant p45 metalloprotease yields have exceeded 4 g/L in *A. oryzae.*

Inhibition of p45 Metalloprotease Activity Using Other Metalloprotease Inhibitors:

Other metalloprotease inhibitors are utilized to further differentiate the p45 metalloprotease from the Bacillus thermolysins. Inhibition constants for 1,10-phenanthroline, phosphoramidon, and $CdCl_2$ are determined to be 130 uM, 1 uM, and 67 uM against the p45 Metalloprotease (Table 3). Inhibition constants for 1,10-phenanthroline, phosphoramidon, and $CdCl_2$ are 85 uM, 26 uM, and 2 uM against the *Bacillus stearothermophilus* thermolysin. All inhibitors are noncompetitive as determined after kinetic analysis with the exception of $CdCl_2$ inhibition of B.s. thermolysin activity which exhibited competitive inhibition. It is of interest to note that phophoramidon is an effective inhibitor of many bacterial metallo-endopeptidases but few of mammalian origin. Also, it is interesting that $CdCl_2$ is found to be such an effective inhibitor of metalloproteases. No evidence of $CdCl_2$ inhibition of metalloproteases has been found in the literature.

TABLE 3

Inhibitor Analysis of the p45 Metalloprotease and Thermolysin from *Bacillus stearothermophilus.*

| | Inhibition Constant ($K_i$) | |
|---|---|---|
| Inhibitor | p45 Maturase | B.s. Thermolysin |
| 1,10-Phenanthroline | 130 uM (Noncompetitive) | 85 uM (Noncompetitive) |
| Phosphoramidon | 1 uM (Noncompetitive) | 26 uM (Noncompetitive) |
| $CdCl_2$ | 67 uM (Noncompetitive) | 2 uM (Competitive) |
| <E-E-I-P-N | no effect ($K_i$ >> 5 mM) | no effect ($K_i$ >> 5 mM) |
| NaCl** | 750 mM | 1500 mM |

**$I_{50}$ values were determined when analyzing the effects of NaCl.

Influence of Heavy Metal Additions to p45 Metalloprotease.

$ZnCl_2$, $CoCl_2$, and $CdCl_2$ are added to purified p45 metalloprotease (0.9 ug) and protease activity is determined using FTC-casein as the substrate. p45 metalloprotease activity is enhanced about 2-fold upon addition of $ZnCl_2$ (0.2 mM), however, no enhanced activity is observed upon addition of $CoCl_2$ (0–4 mM). This result indicates that some apo-p45 metalloprotease may exist in the purified sample. It is interesting that substoichiometric levels of Zn are found after metal analysis (ICP) of the p45 metalloprotease. It appears that zinc levels are only 5% of that expected based on the level of p45 metalloprotease in the sample. No other heavy metal (i.e. Cd, Cr, Co, Cu, Mo, Ni, Li, Zn, Fe, Mn, As, Pb, or Se) is present in the p45 maturase sample.

Deposits of Microorganisms

The following biological materials have been deposited in the Agricultural Research Service Patent Culture Collection (NRRL), Northern Regional Research Center, 1815 University Street, Peoria, Ill., 61604, USA.

| Strain | Accession No. | Deposit Date |
|---|---|---|
| *E. coli* containing pDM120 (p45) (EMCC 0099) | NRRL B-21239 | 4/21/94 |
| *E. coli* containing pSO2 (pyrG) (EMCC 0100) | NRRL B-21240 | 4/21/94 |
| *E. coli* containing pSX233 (EMCC 0101) | NRRL B-21241 | 4/21/94 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122 and under conditions of the Budapest Treaty. The deposit represents a biologically pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. An isolated nucleic acid fragment containing a nucleic acid sequence encoding a metalloprotease obtained from Fusarium having the following characteristics: (a) a molecular weight from about 45,000 daltons to about 50,000 daltons as determined by SDS polyacrylamide gel electrophoresis; (b) functions optimally at a pH between about 8.0 and 11.0; (c) is at least about 10 times more effective than a metalloprotease obtained from *Bacillus stearothermophilus* in converting a proenzyme to an active trypsin-like protease obtained from a strain of *F. oxysporum* deposited at the Deutsche Sammlung von Mikroorganismen, Gottingen, Germany under the number DSM 2672 at a pH between about 6.0 and 7.5 at about 25°–30° C. for about 30–60 minutes; and (d) is less effective than a metalloprotease obtained from *Bacillus stearothermophilus* in cleaving the primary amino groups from casein.

2. The fragment of claim 1 in which said metalloprotease is obtained from a fungus having an N-terminal amino acid sequence depicted in SEQ ID NO:1.

3. The fragment of claim 1 in which said metalloprotease has an N-terminal amino acid sequence depicted in SEQ ID NO:2.

4. The fragment of claim 1 in which said metalloprotease has an amino acid sequence depicted in SEQ ID NO:4.

5. The fragment of claim 1, which comprises the nucleic acid sequence depicted in SEQ ID NO:5.

6. The fragment of claim 1, which comprises the nucleic acid sequence depicted in SEQ ID No:6.

7. A DNA construct comprising the nucleic acid fragment of claim 1.

8. A recombinant vector comprising the DNA construct of claim 7.

9. A recombinant host cell comprising the nucleic acid fragment of claim 1.

10. A method for obtaining a substantially pure metalloprotease obtained from Fusarium having the following characteristics: (a) a molecular weight from about 45,000 daltons to about 50,000 daltons as determined by SDS polyacrylamide gel electrophoresis; (b) functions optimally at a pH between about 8.0 and 11.0; (c) is at least about 10 times more effective than a metalloprotease obtained from *Bacillus stearothermophilus* in converting a proenzyme to an active trypsin-like protease obtained from a strain of *F. oxysporum* deposited at the Deutsche Sammlung von Mikroorganismen, Gottingen, Germany under the number DSM 2672 at a pH between about 6.0 and 7.5 at about 25°–30° C. for about 30–60 minutes; and (d) is less effective than a metalloprotease obtained from *Bacillus stearothermophilus* in cleaving the primary amino groups from casein, which comprises culturing the recombinant host cell of claim 9 under conditions conducive to expression of the metalloprotease, and recovering the metalloprotease from the culture.

11. The method according to claim 10 in which the recombinant host cell is a fungal cell.

12. An isolated nucleic acid fragment containing a nucleic acid sequence encoding a metalloprotease obtained from Aspergillus having the following characteristics: (a) a molecular weight from about 45,000 daltons to about 50,000 daltons as determined by SDS polyacrylamide gel electrophoresis; (b) functions optimally at a pH between about 5.5 and 6.0; (c) is at least about 10 times more effective than a metalloprotease obtained from Bacillus stearothermophilus in converting a proenzyme to an active trypsin-like protease obtained from a strain of *F. oxysporum* deposited at the Deutsche Sammlung von Mikroorganismen, Gottingen, Germany under the number DSM 2672 at a pH between about 6.0 and 7.5 at about 25°–30° C. for about 30–60 minutes; and (d) is less effective than a metalloprotease obtained from *Bacillus stearothermophilus* in cleaving the primary amino groups from casein.

13. The fragment of claim 12 in which said metalloprotease is obtained from a fungus having an N-terminal amino acid sequence depicted in SEQ ID NO:1.

14. The fragment of claim 12 in which said metalloprotease has an N-terminal amino acid sequence consisting of the sequence depicted in SEQ ID NO:3.

15. A DNA construct comprising the nucleic acid fragment of claim 12.

16. A recombinant vector comprising the DNA construct of claim 15.

17. A recombinant host cell comprising the nucleic acid fragment of claim 12.

18. A method for obtaining a substantially pure metalloprotease obtained from Aspergillus having the following characteristics: (a) a molecular weight from about 45,000 daltons to about 50,000 daltons as determined by SDS polyacrylamide gel electrophoresis; (b) functions optimally at a pH between about 5.5 and 6.0; (c) is at least about 10 times more effective than a metalloprotease obtained from *Bacillus stearothermophilus* in converting a proenzyme to an active trypsin-like protease obtained from a strain of *F. oxysporum* deposited at the Deutsche Sammlung von Mikroorganismen, Gottingen, Germany under the number DSM 2672 at a pH between about 6.0 and 7.5 at about 25°–30° C. for about 30–60 minutes; and (d) is less effective than a metalloprotease obtained from *Bacillus stearothermophilus* in cleaving the primary amino groups from casein which comprises culturing the recombinant host cell of claim 17 under conditions conducive to expression of the metalloprotease, and recovering the metalloprotease from the culture.

19. The method according to claim 18 in which the recombinant host cell is a fungal cell.

* * * * *